(12) United States Patent
Takiguchi et al.

(10) Patent No.: US 6,958,045 B2
(45) Date of Patent: Oct. 25, 2005

(54) GAIT DETECTION SYSTEM, GAIT DETECTION APPARATUS, DEVICE, AND GAIT DETECTION METHOD

(75) Inventors: Kiyoaki Takiguchi, Kanagawa (JP); Takaaki Nakamura, Tokyo (JP); Kazuhiko Aida, Tokyo (JP)

(73) Assignee: Sony Corporation, Tokyo (JP)

( * ) Notice: Subject to any disclaimer, the term of this patent is extended or adjusted under 35 U.S.C. 154(b) by 756 days.

(21) Appl. No.: 10/034,454

(22) Filed: Dec. 26, 2001

(65) Prior Publication Data

US 2002/0107649 A1 Aug. 8, 2002

(30) Foreign Application Priority Data

Dec. 27, 2000 (JP) ................................... P2000-396830

(51) Int. Cl.[7] .......................... A61B 5/11; G01C 22/00
(52) U.S. Cl. ...................... 600/595; 702/160; 235/105
(58) Field of Search ........................... 600/587, 592, 600/595; 235/105; 702/160

(56) References Cited

U.S. PATENT DOCUMENTS

| | | | | |
|---|---|---|---|---|
| 4,371,945 A | * | 2/1983 | Karr et al. .................. | 702/160 |
| 5,033,013 A | * | 7/1991 | Kato et al. .................. | 702/160 |
| 5,636,146 A | * | 6/1997 | Flentov et al. .............. | 702/176 |
| 6,052,654 A | * | 4/2000 | Gaudet et al. .............. | 702/160 |
| 6,298,314 B1 | * | 10/2001 | Blackadar et al. .......... | 235/105 |
| 6,493,652 B1 | * | 12/2002 | Ohlenbusch et al. ........ | 702/160 |

* cited by examiner

Primary Examiner—Eric F. Winakur
(74) Attorney, Agent, or Firm—Jay H. Maioli

(57) ABSTRACT

A gait detection apparatus includes a microphone for picking up low-frequency-band sounds which are transmitted through the body of a pedestrian while walking and an analyzer for performing analysis. Accordingly, the gait of the pedestrian is detected. It is also possible to distinguish the gait pattern on the basis of the stance-phase time of a foot sole, the signal intensity, etc. The gait detection apparatus can accurately estimate the step length on the basis of a detected gait cycle, the height of the pedestrian, and signals detected during walking. On the basis of low-frequency-region sounds picked up by the microphone while the pedestrian is walking, the pedestrian can be identified.

10 Claims, 19 Drawing Sheets

FIG. 10

|  | 0Hz | 16Hz | 25Hz | 40Hz | 63Hz | 100Hz |
|---|---|---|---|---|---|---|
| NORMAL WALKING RIGHT LEG | ○ | ○ | ○ | — | — | |
| NORMAL WALKING LEFT LEG | ○ | △ | — | — | — | |
| WALKING UPSTAIRS RIGHT LEG | — | △ | △ | — | — | |
| WALKING UPSTAIRS LEFT LEG | △ | — | — | — | — | |
| WALKING DOWNSTAIRS RIGHT LEG | ○ | — | △ | — | — | |
| WALKING DOWNSTAIRS LEFT LEG | △ | ○ | △ | — | — | |
| STANDING ON TRAIN | — | — | — | — | — | |

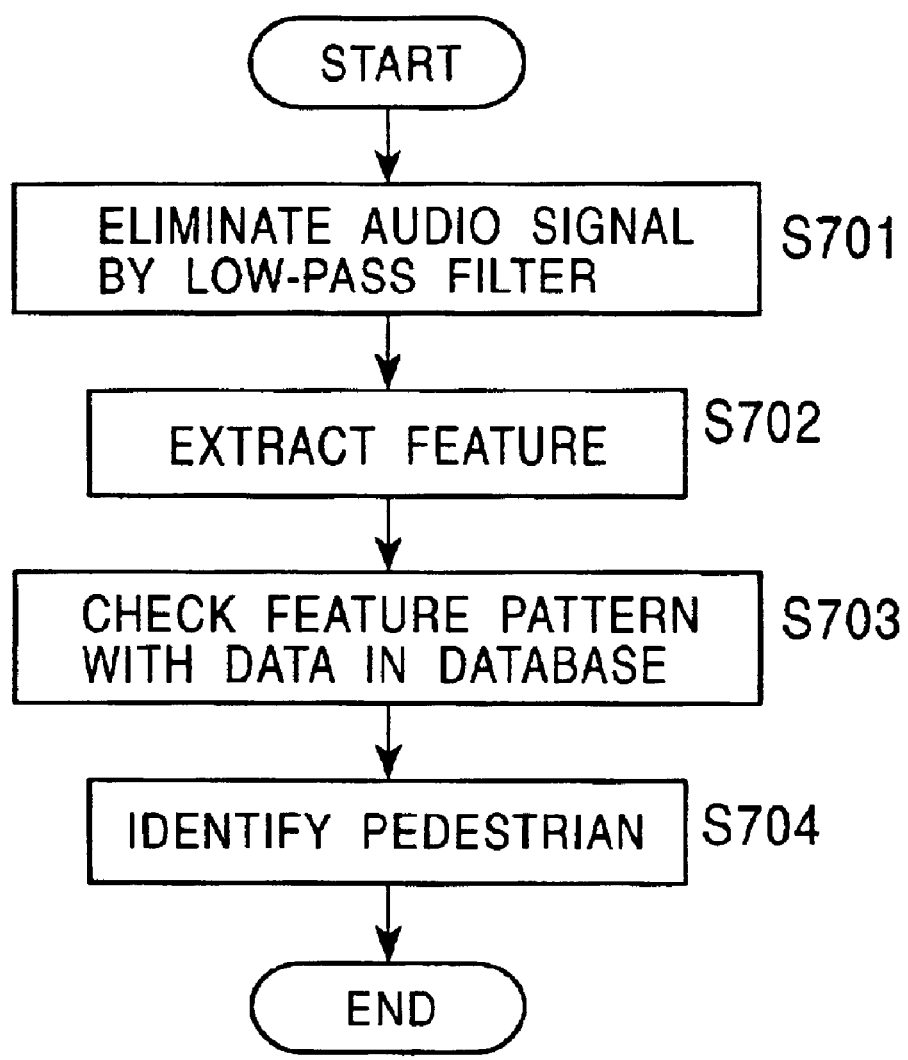

GAIT DETECTION SYSTEM, GAIT DETECTION APPARATUS, DEVICE, AND GAIT DETECTION METHOD

BACKGROUND OF THE INVENTION

1. Field of the Invention

The present invention relates to gait detection systems, gait detection apparatuses, devices, and gait detection methods.

2. Description of the Related Art

One type of gait detection system includes a so-called pedometer system which employs a built-in pendulum and which detects the motion of the pendulum during walking.

Another gait detection system employs, instead of a pendulum, an acceleration sensor and a gyro sensor to detect motion (movement) on the basis of the acceleration detected by these sensors, whereby the gait of the user can be detected.

The gait of a pedestrian detected by the foregoing methods is used to simply count the steps as in a pedometer and to estimate the distance traveled by the pedestrian on the basis of the detected gait. This is used to provide a so-called autonomous navigation capability in a navigation system using a Global Positioning System (GPS) in which the position determined on the basis of electromagnetic waves transmitted from a GPS satellite is corrected on the basis of the distance traveled by the pedestrian. Hitherto, in such a case, the pedestrian's step length is estimated by utilizing the correlation of the step length with two parameters, namely, the walking frequency, i.e., the number of steps per unit time, and the height.

Another technology for identifying the person or animal being detected on the basis of the detected gait is proposed. In this case, the technology may employ the foregoing systems and a system for detecting the gait by detecting footsteps. For example, a microphone is used to pick up hoofbeats generated when a horse's hooves make contact with the ground, and the horse is identified on the basis of the gait which can be detected from the sound of hoofs (see Japanese Unexamined Patent Application Publication No. 2000-193520).

The foregoing detection systems have the following problems:

In the mechanical system such as the pedometer using the built-in pendulum, even when a pedestrian is not walking, the motion in response to even slight pendulum movement may be counted as one step. Accordingly, the measurement accuracy is reduced.

In both the system using the built-in pendulum and the system using the acceleration sensor and the gyro sensor, a detection device must be placed at a specific location such as the waist of a pedestrian in order to improve the detection accuracy. In the system using the acceleration sensor and the gyro sensor, the device must be placed on the pedestrian, and the axial direction of the sensors must be detected, since the detection results depend on the sensor directions. Such detection is time-consuming, and the program and circuit configurations become complicated. A multi-axial acceleration sensor is necessary to detect the complex gait activity of a pedestrian. As a result, the configuration becomes more complex, and the cost is increased.

When detecting vibrations by the acceleration sensor and the gyro sensor or when detecting the gait on the basis of the sound picked up by the microphone, each step is detected by processing a detected waveform. In this case, a method for simply counting the peaks of waveforms generated during walking may be employed. Another method converts time-series variations in waveforms into a frequency intensity spectrum pattern by subjecting the variations to Fourier transform or wavelet transform. The method analyzes the pattern, thereby detecting the gait.

In an actual environment for detecting the gait, when a pedestrian is in a vehicle, the microphone picks up noise made by the vehicle and extraneous noise other than that made by the pedestrian. In any of the foregoing methods, the detection accuracy or the analysis accuracy is greatly influenced by the noise. In addition, when detecting the gait of a human being, it is impossible to analyze the gait on the basis of the sound picked up by the microphone and to identify the person (pedestrian) because of the extraneous noise pickup.

To say nothing of a case in which the peaks of waveforms are simply counted, when a waveform is subjected to Fourier transform, the information loses its time component. It is thus impossible to accurately detect various gait patterns of a pedestrian, such as trotting, walking upstairs and downstairs, and the like. A waveform is subjected to wavelet transform by presetting the duration required for making one step, extracting a detection waveform by a windowing function having a duration longer than the duration for one step, and performing frequency analysis of the waveform, whereby a frequency spectrum for one step is obtained. This processing is cumbersome. When the duration for making one step is longer than the preset operation duration or windowing function, the processing may become erroneous.

When estimating the distance traveled by a pedestrian on the basis of the gait of the pedestrian, step length is estimated from the pedestrian's gait and height. Known detection systems lack satisfactory detection accuracy in gait detection. When the gait of the pedestrian shows a pattern differing from the normal gait, that is, when the pedestrian walks with long strides, trots, or walks upstairs and/or downstairs, it is difficult to identify who the pedestrian is. It is also difficult to accurately detect the step length and to accurately estimate the distance traveled.

When a device including a wristwatch is provided with a gait detection function, the size may be increased and the configuration may become complex because the foregoing systems require that a pendulum, an acceleration sensor, a gyro sensor, and the like be added to the device.

SUMMARY OF THE INVENTION

Accordingly, it is an object of the present invention to provide a gait detection system, a gait detection apparatus, a device, and a gait detection method capable of detecting the gait with high accuracy.

In order to achieve the foregoing objects, a gait detection system in accordance with an aspect of the present invention includes a microphone for picking up vibrations generated when a pedestrian walks. Of electrical signals obtained from the vibrations, an analyzer analyzes variations in signals corresponding to a predetermined frequency or less, whereby the gait of the pedestrian is detected and gait information is generated. The gait information can be output by an output unit using characters or sound.

The vibrations generated by a pedestrian during walking include vibrations transmitted through the body of the pedestrian and sound transmitted through the air or the body during walking.

In the gait detection system, the microphone, the analyzer, and the output unit may be integrated into a single apparatus.

Alternatively, it may be structured such that only the microphone which is to be placed on the pedestrian is separate from the analyzer and the output unit; and the analyzer and the output unit may form a gait detection apparatus. In this case, signals can be transmitted between the microphone and the analyzer via a connecting cord or wireless communication means using electromagnetic waves or infrared rays.

When the pedestrian walks, characteristic vibrations, which result from foot-strike impact, stance-phase impact, and transmission of motions to foot joints, bones, and muscles, are generated in frequency regions less than or equal to 100 Hz during walking. Since these vibrations are transmitted through the body of the pedestrian, the vibrations are picked up by the microphone. To this end, it is preferable that the microphone be placed in close vicinity to the pedestrian's body.

The simplest gait information obtained by analyzing the electrical signals output from the microphone includes the number of steps taken by the pedestrian.

When the electrical signals output from the microphone are converted into a frequency intensity spectrum pattern or spectrogram, the obtained frequency intensity spectrum pattern includes a self-organized, complex temporal/frequency/intensity pattern as in a voice formant structure or voice print which results from foot-strike impact, stance-phase impact, and transmission of motions to foot joints, bones, and muscles. Using the pattern, the pedestrian's gait pattern including walking at a fast pace and walking upstairs/downstairs can be detected. It is also possible to differentiate among a plurality of pedestrians.

Such detection can be performed by referring to the stance-phase duration which begins with heal strike and ends with toe-off, the foot-strike impact, the timing for the contact of the heel or toe with the ground, the force of ground-contact made with the heal or toe, etc. To this end, it is effective to analyze a signal by the analyzer on the basis of at least one of the duration and the frequency intensity of a signal in a frequency band less than or equal to 100 Hz.

When a data storage unit stores beforehand signal data corresponding to gait model patters of a plurality of pedestrians and signal data corresponding to various gait model patterns including normal gait, walking at a fast pace, and walking upstairs/downstairs of each pedestrian, signal analysis can be performed by comparing a signal pattern with the signal data stored in the data storage unit and determining whether or not the signal pattern matches the stored signal data. Accordingly, the gate pattern can be specified. Also, so-called person authentication to specify a pedestrian or to determine whether or not the pedestrian being detected is a registered pedestrian can be performed.

When the analyzer detects the gait cycle, the pedestrian's step length can be estimated on the basis of the gait cycle and the pedestrian's height which is input in advance. Furthermore, the distance traveled by the pedestrian can be estimated from the step length and the number of steps.

Alternatively, when analyzing signals by the analyzer, only signals in a characteristic frequency band in which vibrations are generated during walking can be used. The analyzer may analyze the signals on the basis of the presence of the signals in the characteristic frequency band or the intensity of the signal. In this case, a filter may be provided to allow signals in the characteristic frequency band to pass through. Preferably, the characteristic frequency band is 100 Hz or less, or more specifically 40 Hz or less.

The present invention includes a microphone, an analyzer, and a display unit for outputting gait information detected by the analyzer using characters. The present invention can be regarded as a device to be placed on the body of a user or on the clothes the user is wearing. The device may be a wristwatch, a wristwatch-type pedometer, or the like.

As described above, according to the present invention, vibrations (sounds) in low frequency regions are picked up and analyzed, thereby detecting the gait of a pedestrian with high accuracy.

BRIEF DESCRIPTION OF THE DRAWINGS

FIG. 10 is an example of a determination table used in the gait detection apparatus shown in FIG. 9;

FIG. 18 is a flowchart showing a process of authenticating a person; and

DESCRIPTION OF THE PREFERRED EMBODIMENTS

The present invention will be described in detail using first to third embodiments illustrated by the accompanying drawings.

First Embodiment: Gait Detection

Figure 1:
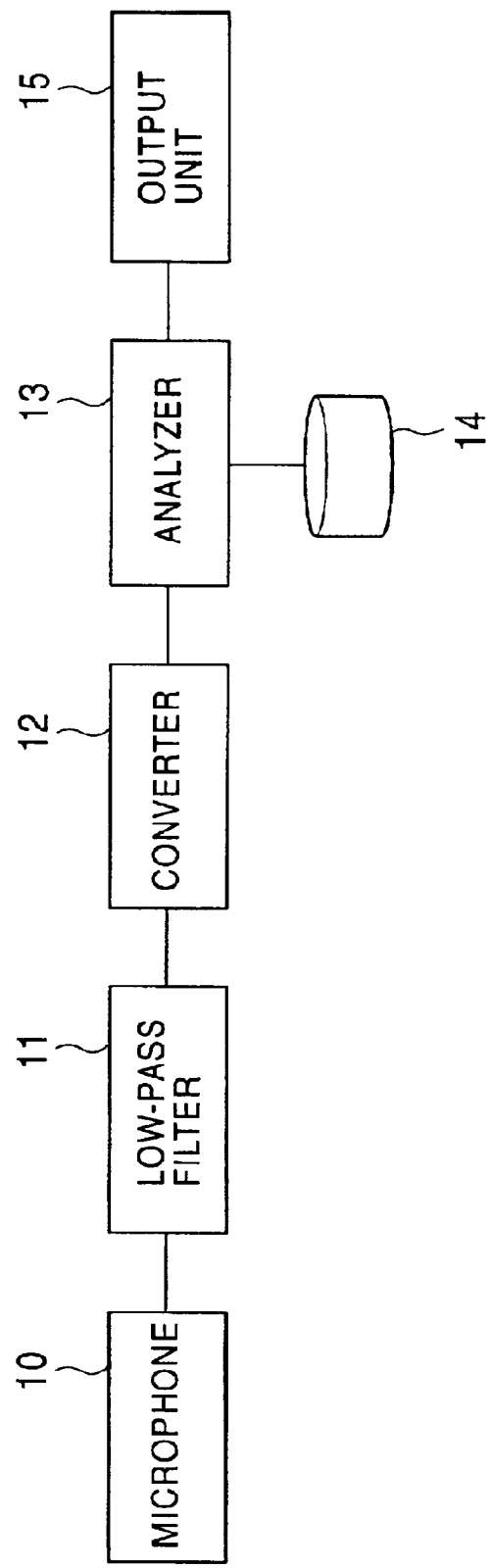
FIG. 1 is a block diagram showing the structure of a gait detection apparatus according to a first embodiment of the present invention.

FIG. 1 shows the basic structure of a gait detection apparatus or gait detection system according to a first embodiment of the present invention. Referring to FIG. 1, the gait detection apparatus includes a microphone 10 for picking up ambient sound and converting the ambient sound into an electrical signal; a low-pass filter 11 for only allowing a signal at a frequency less than or equal to a predetermined frequency to pass through; a converter 12 for A/D-converting the sound having passed through the low-pass filter 11 into a digital waveform; an analyzer or detector 13 for analyzing the waveform obtained by the converter 12 and detecting the gait; a database or data storage unit 14 for storing data used in analysis by the analyzer 13; and an output unit 15 such as a monitor for outputting the detection result obtained by the analyzer 13 using visual information such as characters.

The microphone 10 picks up vibrations or sounds in all the collectable frequency bands. By collecting the ambient sound using the microphone 10, vibrations which are generated while a pedestrian is walking and which are transmitted through the pedestrian's body and sound transmitted through the air are picked up. Generally, a microphone of a cellular-phone-type terminal employs a band-pass filter to eliminate signals in frequency bands including 20 Hz or less and 20000 Hz or greater outside the audible region. In the first embodiment, a signal output from the microphone 10 is input to the low-pass filter 11 which only allows a signal at a predetermined frequency or less, such as 200 Hz or less, to pass through, thereby isolating the signal from a so-called audio signal, that is, a frequency component higher than 200 Hz. The analyzer 13 analyzes the component signal at the predetermined frequency or less.

The basic concept of analysis by the analyzer 13 on the basis of the sound picked up by the microphone 10 will now be described.

Figure 2:
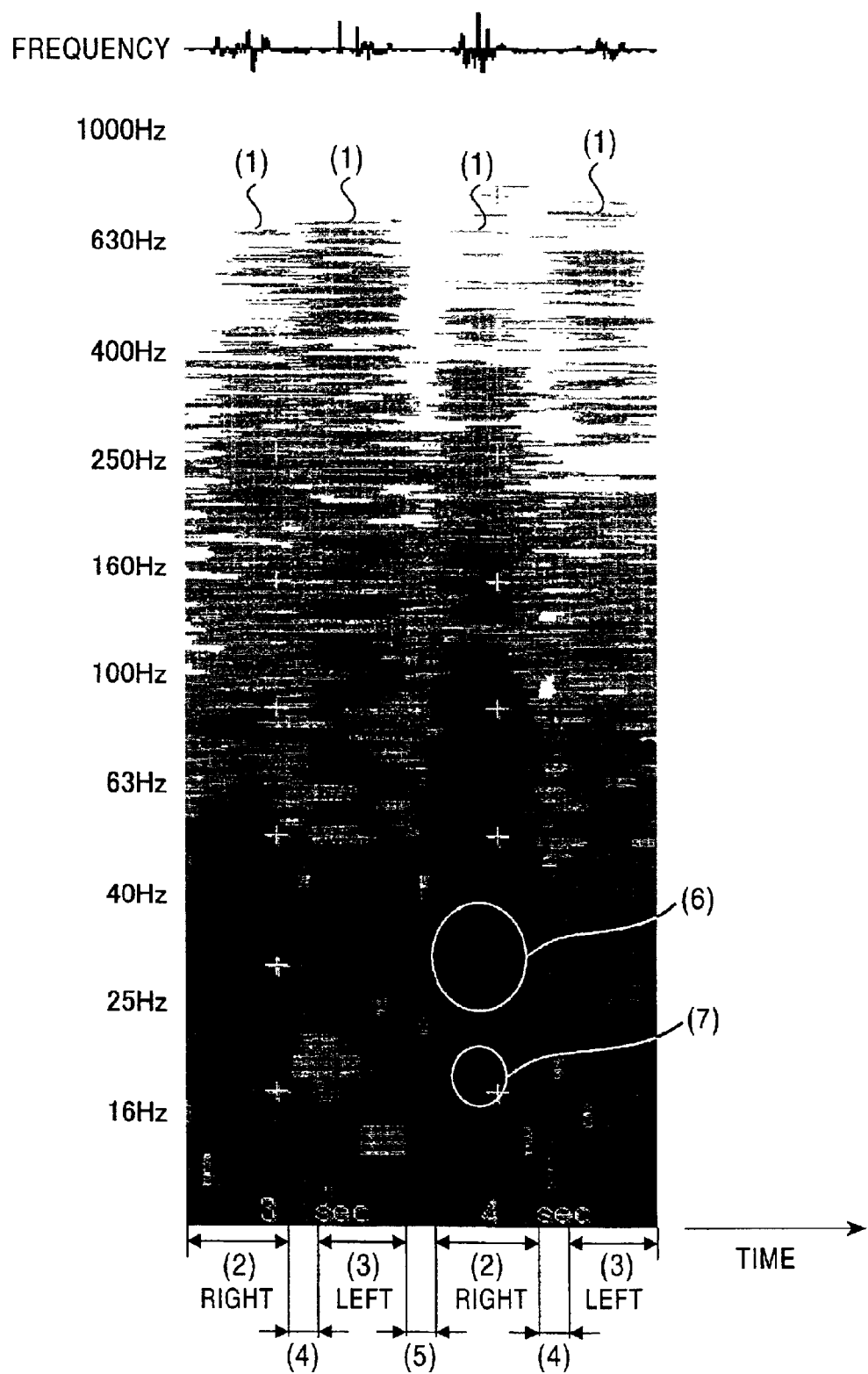
FIG. 2 is an example of a spectrogram obtained from a series of signals obtained from a pedestrian during walking.

Specifically, when the pedestrian walks, vibrations are generated by the pedestrian making ground-contact with, alternately, the left leg and the right leg. The microphone 10 picks up the vibrations, and the vibrations are subjected to A/D conversion by the converter 12, thereby outputting digital signals. The output signals, that is, the voltages, are subjected to wavelet transform. Referring to FIG. 2, the results of the wavelet transform are shown in a spectrogram illustrating the frequency intensity spectrum pattern.

The spectrogram shown in FIG. 2 is obtained when one pedestrian walks at a normal pace. The "normal" gait means that the pedestrian does not walk at a quick pace or a slow pace; the pedestrian walks while not being aware of the pedestrian's pace. As shown in FIG. 2, when a human being walks, a characteristic temporal/frequency/intensity pattern is generated at 100 Hz or less, which is near the lower limit of the audible range (approximately from 20 to 20000 Hz), that is, more specifically, in the vicinity of a low frequency band at 30 to 40 Hz or less, as a result of foot-strike impact, stance-phase impact, and transmission of motions to the waist, the hip joint, the knee joints, the ankle, the toes, bones, and muscles. In the first embodiment, the low frequency band component pattern is analyzed to detect the gait.

The human gait can be divided into two phases: the stance phase and the swing phase. The stance phase begins after heel strike and ends with toe off. The swing phase begins after toe off and ends with the contact with the ground.

The stance phase starts with the contact of the foot sole with the ground at the heel, goes through the lateral side of the foot (lateral longitudinal arch of foot), and changes the direction at the root of the little finger (fifth metatarsal bone), and ends with the root of the thumb (first metatarsal bone). The cycle is repeated. The ground impact in the stance phase is absorbed by each joint, muscles, and panniculus adiposus. Part of the low frequency component resonates with the absorbed impact, and the resonance is transmitted through the body, resulting in the low-frequency-band vibration having a complex temporal/frequency/intensity pattern, as shown in the spectrogram in FIG. 2.

Using the example of the pedestrian shown in FIG. 2, the low frequency band component generated during walking are examined in detail. Referring to FIG. 2, portions (1) have clear peaks, each peak corresponding to each step.

Examining the spectrogram shown in FIG. 2 in fuller detail, portions (2) in the horizontal direction each represent the stance-phase time of the right leg; portions (3) each represent the stance-phase time of the left leg; portions (4) each represent the gap time during which the leg touching the ground changes from the right leg to the left leg; and portion (5) represents the gap time during which the leg touching the ground changes from the left leg to the right leg. The gait of the pedestrian can be characterized by temporal features including the time periods represented by portions (2) to (5).

Figure 3:
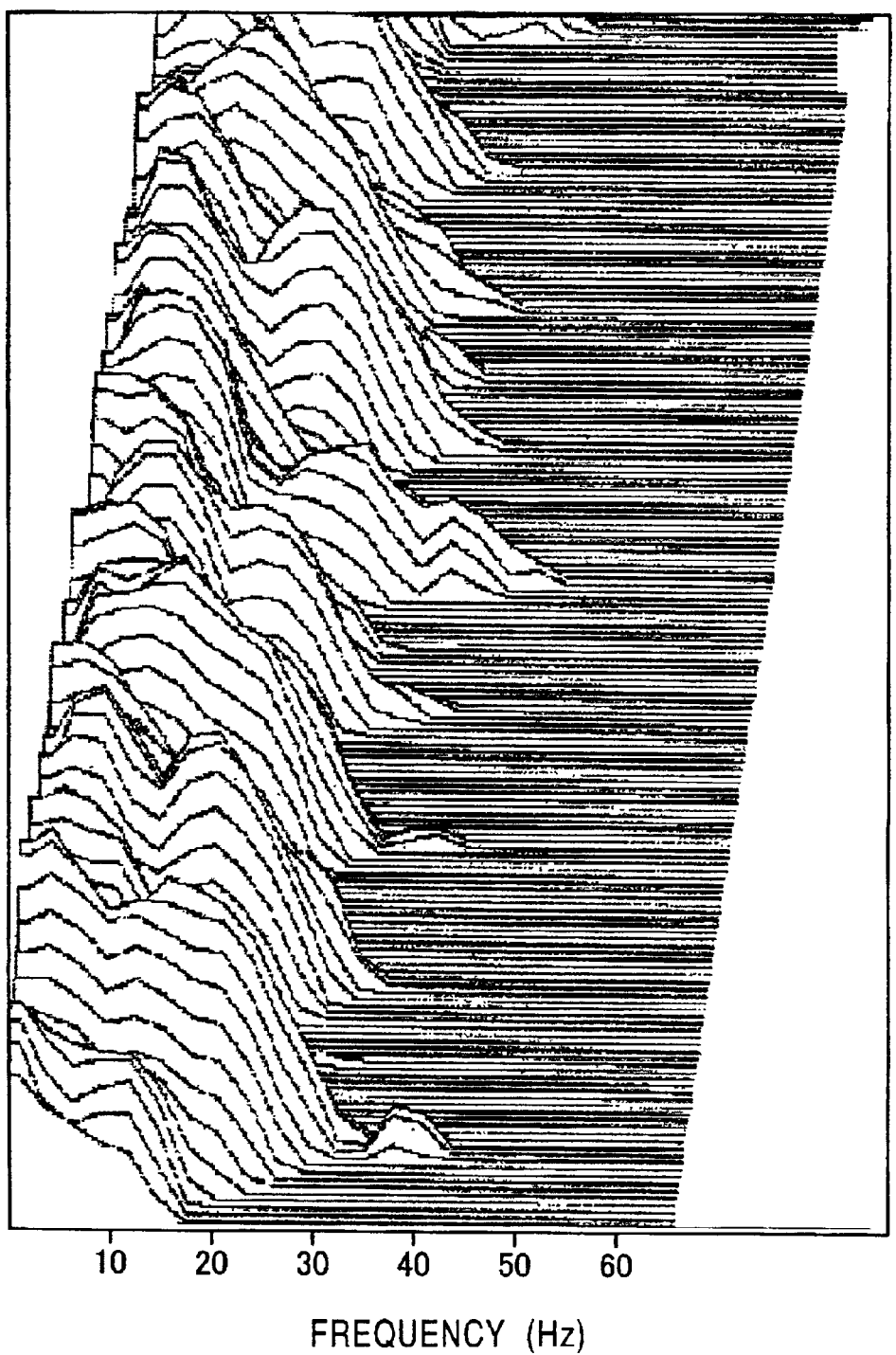
FIG. 3 illustrates a three-dimensional spectrogram of the spectrogram shown in FIG. 2.

The spectrogram shown in FIG. 2 is examined from the point of view of the frequency intensity. In the spectrogram, the darker the color is, the higher the frequency intensity is; the lighter the color is, the lower the frequency intensity is. FIG. 3 is a three-dimensional spectrogram showing the spectrogram shown in FIG. 2. Referring to FIG. 3, the higher the spectrogram rises, the higher the frequency intensity is. Referring back to FIG. 2, the spectrogram showing each step is examined. The frequency intensity is especially high in portions (6) and (7). Though there may be differences between individuals, the frequency intensity is high in portion (6) as a result of the vibration (sound) caused by the contact of the heel with the ground; and the frequency intensity is high in portion (7) as a result of the vibration (sound) caused by the contact of the toe with the ground. During walking, the heel makes contact with the ground prior to the toe contact. Thus, strictly speaking, there is a time difference between portions (6) and (7).

Referring to FIG. 2, the frequency intensity of the left leg is lower than that of the right leg because the pedestrian is right-footed, the microphone 10 is set at the right side, etc. In general, the dominant leg has a higher frequency intensity than that of the other leg. In such a case, when the microphone 10 is set at the dominant leg side, the frequency intensity of the other leg, which is apart from the microphone 10, may be very weak.

Figure 4:
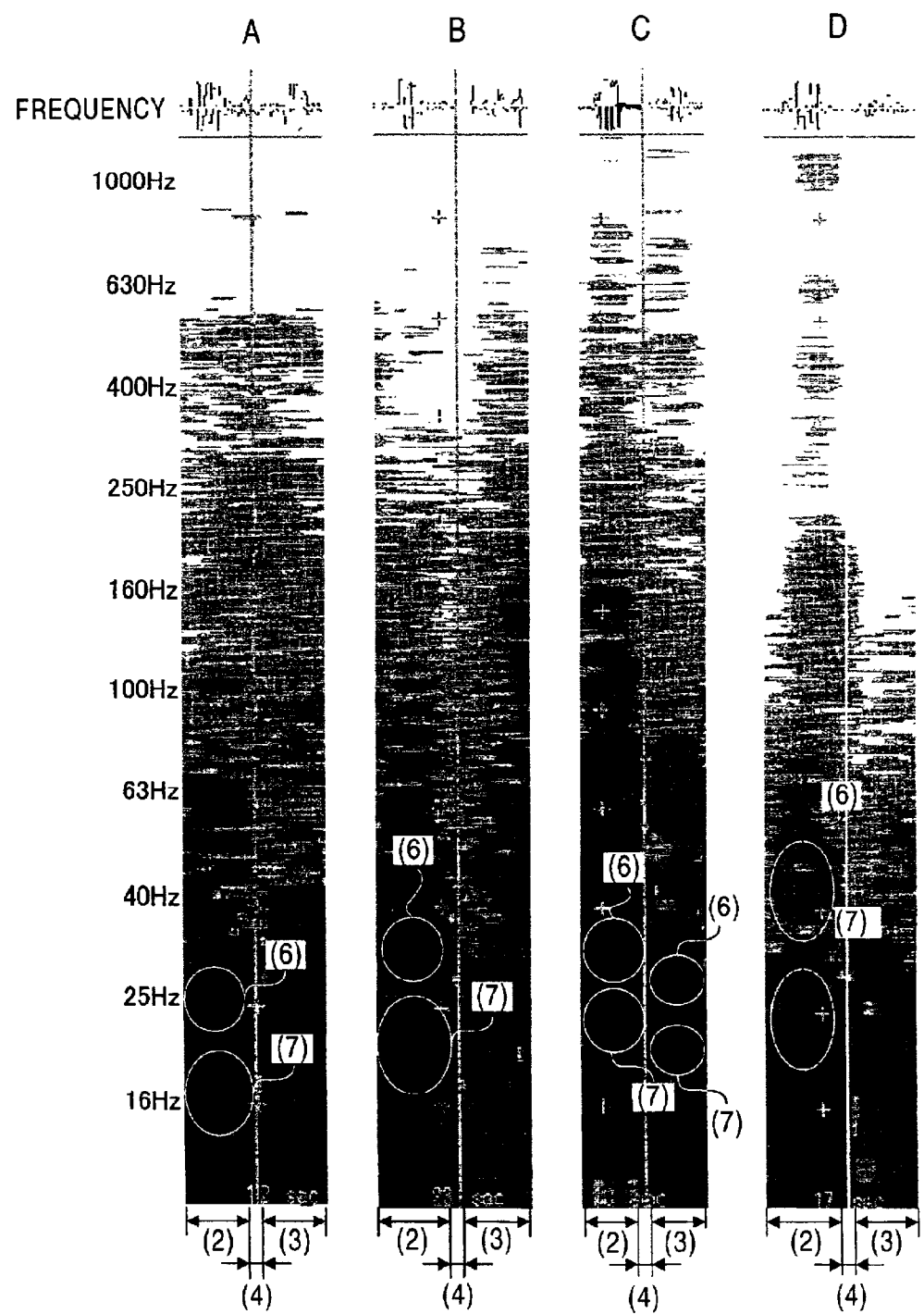
FIG. 4 includes spectrograms of a plurality of pedestrians, including spectrogram A showing a first example; spectrogram B showing a second example; spectrogram C showing a third example; and spectrogram D showing a fourth example.

Each pedestrian has his/her own spectrogram feature points. Spectrograms shown in FIG. 4 represent a plurality of pedestrians A, B, C, and D during normal walking. These spectrograms show feature points in portions (1) to (7), which are similar to those shown in FIG. 2. The time periods shown in portions (2), (3), and (4) and the frequency bands and intensities shown in portions (6) and (7) differ among different pedestrians.

Figure 5:
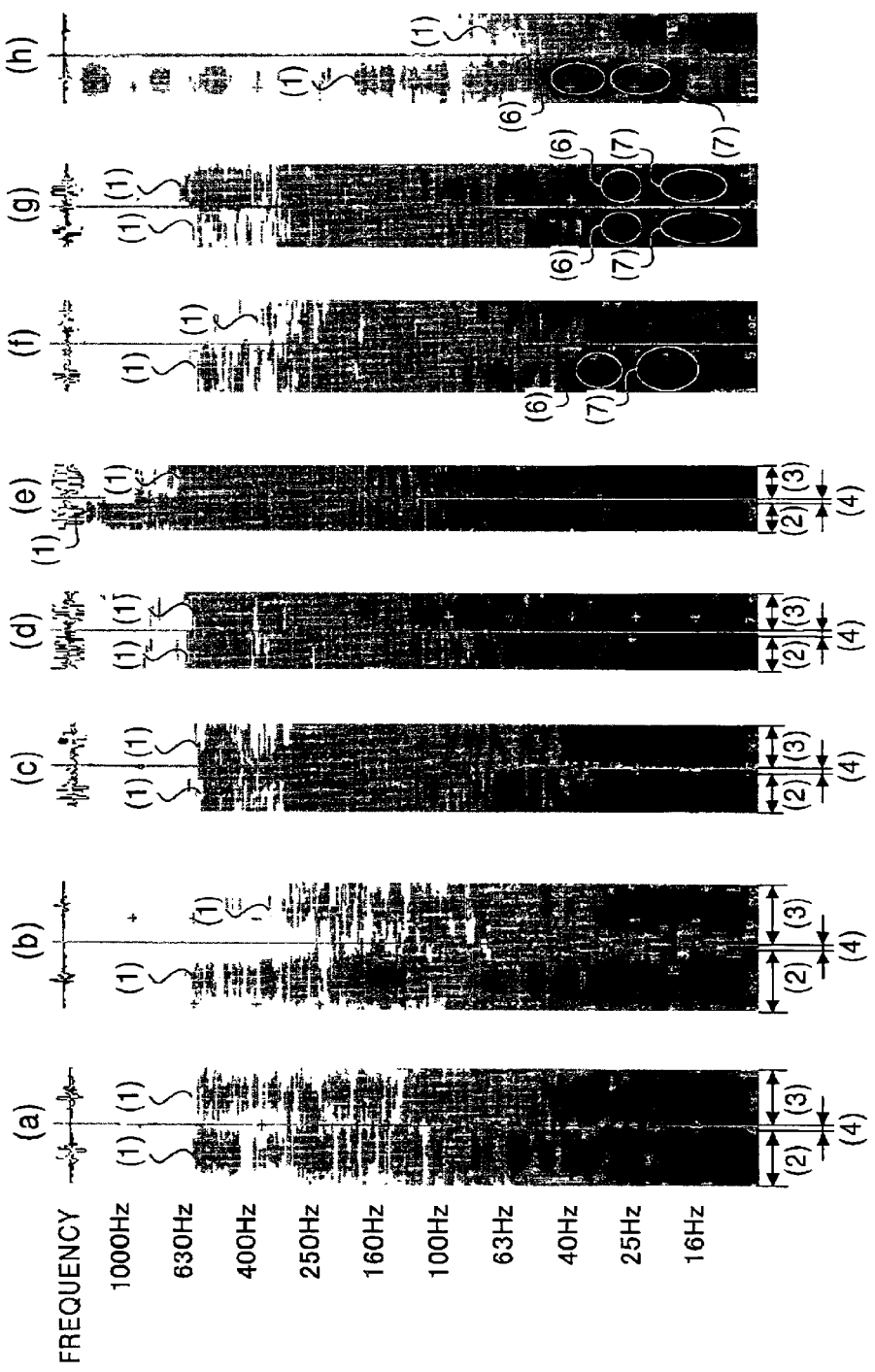
FIG. 5 includes spectrograms of various gait patterns of a single pedestrian, including part (a) showing the pedestrian marking time at one place; part (b) showing the pedestrian walking at a slow pace; part (c) showing the normal gait; part (d) showing the pedestrian walking at a fast pace; part (e) showing the pedestrian jogging; part (f) showing the pedestrian walking upstairs; part (g) showing the pedestrian walking downstairs; and part (h) showing the pedestrian walking on a train.

FIG. 5 includes spectrograms of various gait patterns of a single pedestrian. Part (a) shows a spectrogram of the pedestrian marking time at one place; part (b) shows a spectrogram of the pedestrian walking at a slow pace; part (c) shows a spectrogram of the pedestrian walking at a normal pace; part (d) shows a spectrogram of the pedestrian walking at a fast pace; part (e) shows a spectrogram of the pedestrian jogging; part (f) shows a spectrogram of the pedestrian walking upstairs; part (g) shows a spectrogram of the pedestrian walking downstairs; and part (h) shows a spectrogram of the pedestrian walking on a train.

When these spectrograms are compared with one another, parts (b), (c), and (d) in which the gait cycles are different have different stance-phase time periods shown in portions (2) and (3) (the faster the pedestrian walks, the shorter the stance phase becomes).

In part (e) showing the pedestrian jogging, compared with the other parts, the range of the high frequency intensity is stretched to a high frequency region. Also, the peak frequency of the signal (portion (1)) is high.

In part (f) showing the pedestrian walking upstairs, the frequency intensities in portions (6) and (7) at the time the foot makes ground contact are weak. Because the pedestrian raises the leg and then the foot touches a stair surface, the ground impact is weaker than that during normal walking on a flat surface. When walking upstairs, the toe contact is primary; the frequency intensity in portion (6) at the time the heel makes contact with the ground is weak. Comparing walking upstairs and downstairs in parts (f) and (g) with each other, the band is stretched to a high frequency band especially during walking downstairs. This indicates that, in accordance with the impact on the foot, the energy spectrum is generated in a high frequency band. When walking downstairs as shown in part (g) in FIG. 5, the toe makes contact with the ground prior to the heel contact. Thus, the frequency intensity in portion (7) at the time the toe makes contact with the ground is strong.

As shown in part (h) in FIG. 5, the pedestrian walking on a train, which has been difficult to detect in the past, can be detected. In this case, the signal peak shown in portion (1) is much lower than the others, and the frequency intensities shown in portions (6) and (7) at the time the heal and toe make ground contact are much lower than the others. On the basis of these points, it can be concluded that the pedestrian is walking with caution. Most of the external noise is higher than the frequency bands shown in FIG. 5. Thus, features can be extracted without being obstructed by the noise.

As described above, examples of various processes of detecting the gait and the gait pattern on the basis of signals obtained from the vibrations (sounds) during walking picked up by the microphone 10 will now be described.

Figure 6:
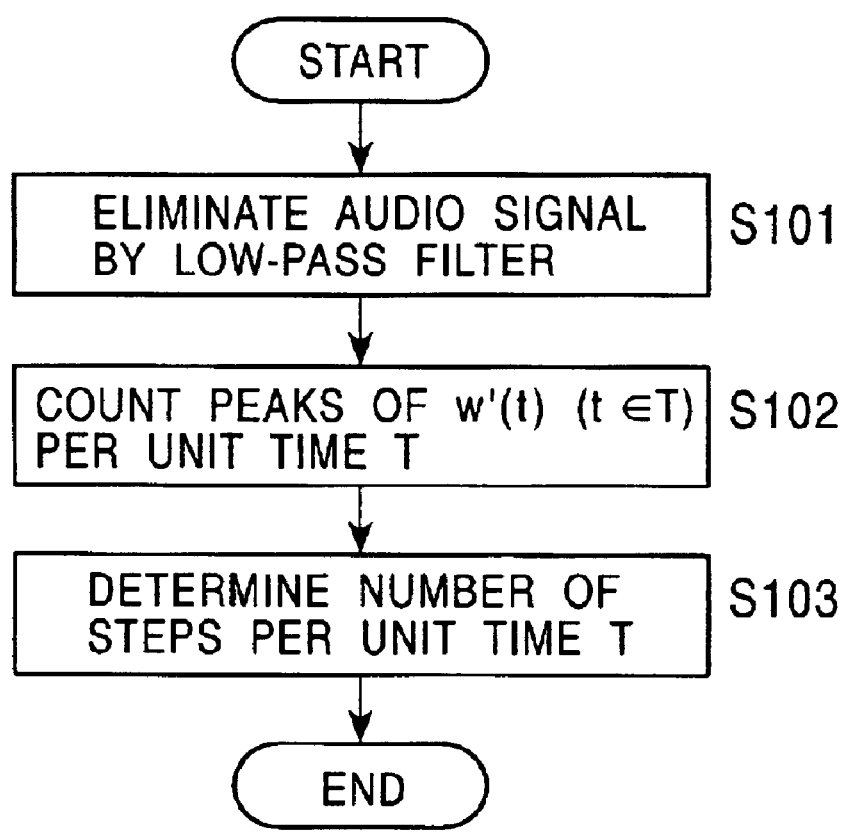
FIG. 6 is a flowchart showing a process of detecting the number of steps.

FIG. 6 shows a process of detecting the number of steps per unit time on the basis of peaks (1) in the spectrogram shown in FIG. 2.

The process eliminates signals at or higher than a predetermined frequency, that is, normal audio signals, using the low-pass filter 11 from signals w(t) obtained by converting, by the converter 12, signals output from the microphone 10, and the process obtains signals w'(t) (step S101) wherein t represents the time (variable).

The analyzer 13 counts the number of peaks of the signals w'(t) for unit time T (which is arbitrary set) (step S102) wherein t∈T.

As a result, the number of steps per unit time T is determined on the basis of the number of peaks per unit time T (step S103). When the number of steps per unit time T is detected, the gait pattern can be determined, this is whether the pedestrian is walking at a normal pace or walking at a fast pace.

Subsequently, the output unit 15 outputs information including the detected number of steps per unit time T.

As can be understood from the spectrogram in FIG. 2, the normal gait in the stance phase has a band-shaped pattern in a broadband, ranging from a low frequency outside the audible range to the audible range, for approximately one second per step. The band-shaped temporal/frequency/intensity pattern includes different frequency intensity spectra for portions of the foot sole in accordance with the corresponding portions' contacts with the ground.

Figure 7:
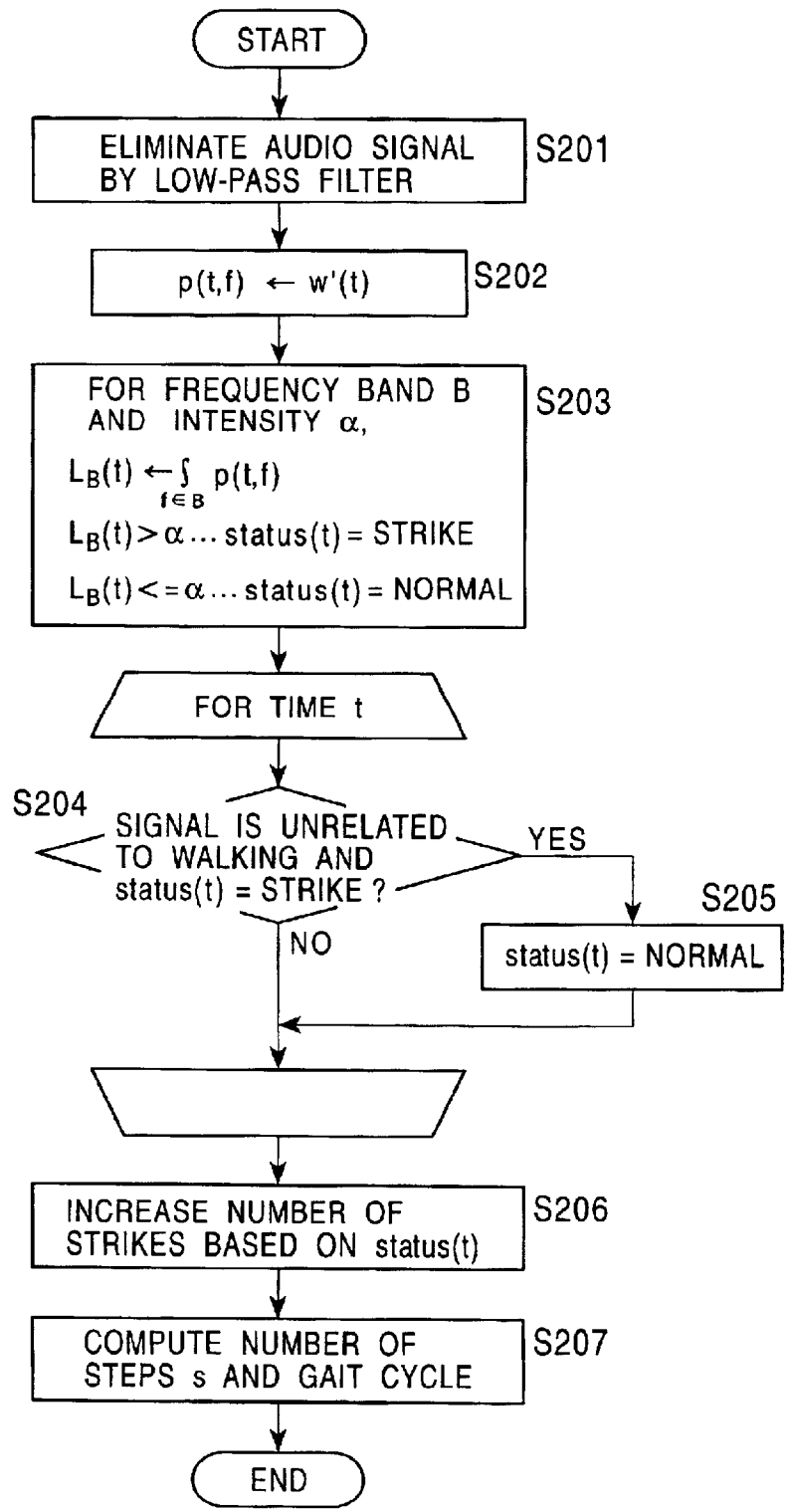
FIG. 7 is a flowchart showing another process of detecting the number of steps.

FIG. 7 shows a process of computing the number of steps per unit time on the basis of the foot sole's stance-phase duration per step (portions (2) and (3) in FIG. 2) obtained from the temporal/frequency/intensity pattern in the spectrogram. As shown in FIG. 2, the frequency intensity is maintained for a predetermined period of time or longer in accordance with the time during which the left and right foot soles are in contact with the ground. The temporal/frequency/intensity spectrogram illustrates the pedestrian's feature pattern. On the basis of these facts, the number of steps per unit time and the gait cycle are detected. On the basis of the temporal/frequency/intensity features, it is possible to distinguish the impact made by factors other than walking, such as the impact made by the pedestrian's hand hitting the body, and the external noise caused by a vehicle or the like from sound caused by walking. The database 14 stores beforehand data for the temporal/frequency/intensity spectrogram.

From the signals w(t) obtained by subjecting the signals from the microphone 10 to A/D conversion by the converter 12, the low-pass filter 11 eliminates signals at or higher than a predetermined frequency, that is, normal audio signals, and obtains the signals w'(t) (step S201).

The analyzer 13 converts the signals w'(t) into a relational expression p(t, f) of the time and the frequency intensity (step S202).

The relational expression p(t, f) is integrated relative to a predetermined frequency band B, and the pedestrian status is determined on the basis of the relationship with a frequency intensity $\alpha$. When the integration value $L_B(t)$ is greater than the frequency intensity $\alpha$, the pedestrian status (status(t)) is "strike". When the integration value $L_B(t)$ is less than or equal to the frequency intensity $\alpha$, the pedestrian status is "normal", that is, a state which is not "strike" (step S203).

Every time a new signal is input per micro time, processing in step S204 is performed. In step S204, the process determines whether or not a signal at time t at that time is unrelated to walking, that is, whether or not the signal includes no feature points (pattern and intensity distribution) which are characteristic of walking. Also, the process determines whether or not the pedestrian status is determined as "strike" in step S203 (step S204). As a result, when these conditions are satisfied, it is determined that the process has made a mistake in determination. The process changes the pedestrian status to "strike" (step S205). If the conditions in step S204 are not satisfied, the pedestrian status is maintained.

Accordingly, every time a signal is input, the pedestrian status(t) at that time is determined. If the pedestrian status has been changed from the previous status (t−1) from "normal" to "strike", the number of strikes is increased by one (step S206).

When the number of strikes per unit time is computed on the basis of the counted number of strikes, the number of steps s per unit time can be detected. By dividing unit time by the number of steps s, the gait cycle can be detected (step S207).

Compared with the process of simply detecting peaks of signals shown in FIG. 6, the process in FIG. 7 can specifically detect the stance-phase duration per step. It is thus possible to obtain more accumulate, applicable information.

A case in which the pedestrian's gait pattern is recognized from sound picked up by the microphone 10 on the basis of features of various gait patterns as shown in FIG. 5 will now be described. In this case, the database 14 stores therein beforehand data for feature points of various gait patterns.

Figure 8:
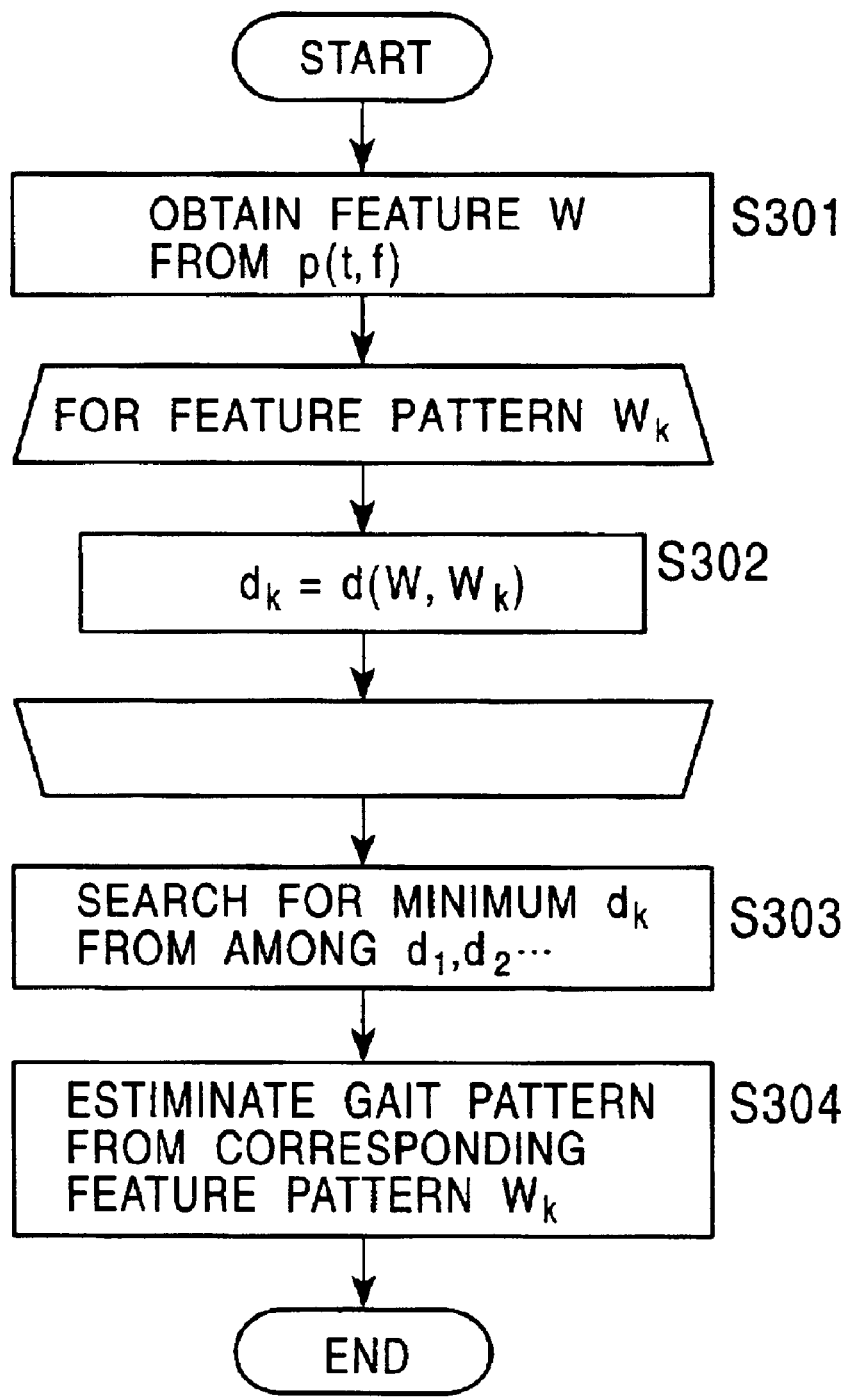
FIG. 8 is a flowchart showing a process of estimating the gait pattern.

As shown in FIG. 8, the analyzer 13 obtains a feature pattern W of the detected gait from the relational expression p(t, f) of the time and the frequency intensity, which is obtained in a manner similar to steps S201 and S202 in FIG. 7 (step S301).

For the obtained feature pattern W, reference is made to the database 14, and pattern recognition processing with various feature patterns $W_k$, such as feature pattern $W_1$ at a slow pace, feature pattern $W_2$ at a normal pace, feature pattern W3 at a fast pace, etc, is performed. For example, Mahalanobis distance between the feature pattern W and each feature pattern $W_k$ stored in the database 14 is computed, and a difference $d_k$ with the feature pattern W is obtained (step S302).

The minimum difference $d_k$ is retrieved from among differences $d_k$ with feature patterns $W_k$ (step S303), and the pedestrian's gait pattern is estimated on the basis of the feature pattern $W_k$ having the minimum $d_k$ (step S304).

With the above-described gait detection apparatus, the microphone 10 picks up low-frequency-band components transmitted through the body during walking, and the gait is detected on the basis of the sound. By detecting the gait on the basis of the low-frequency-band components, the low-frequency-band components can be reliably distinguished from other noise. As a result, highly accurate detection results can be obtained.

By analyzing the detected vibrations, the gait patterns can be distinguished from one another on the basis of the stance-phase duration of the foot sole, the frequency intensity, etc. From the second step onward, variations in the pedestrian's pace can be detected in real time.

Since the microphone 10 is used instead of an acceleration sensor or a gyro sensor which has been used in the past, the gait detection apparatus has a merit in that it consumes less electricity.

The foregoing gait detection processes are implemented by the apparatus as configured in FIG. 1. Alternatively, the simplified structure includes a gait detection apparatus shown in FIG. 9.

Figure 9:
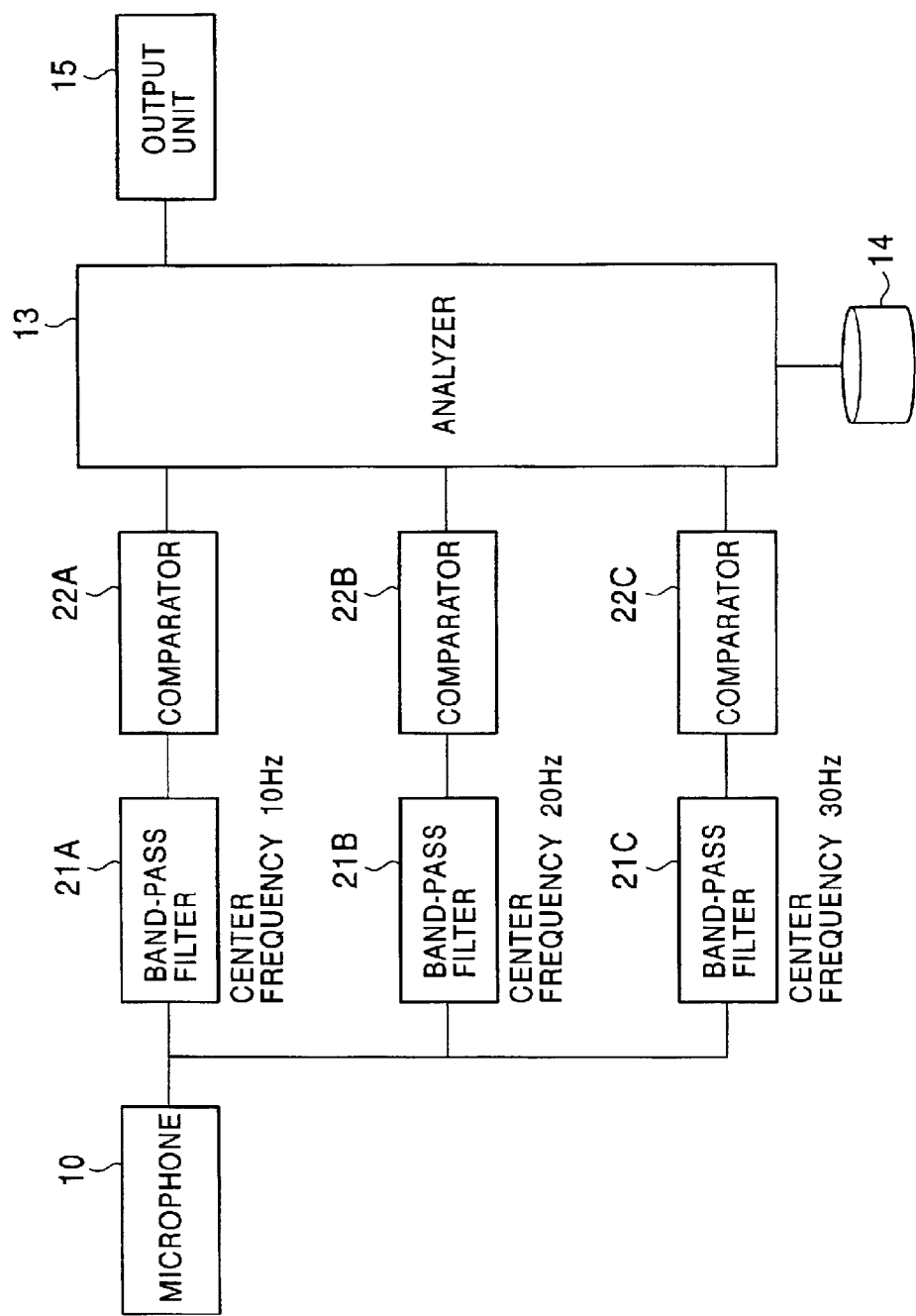
FIG. 9 is a block diagram of another example of a gait detection apparatus.

The gait detection apparatus shown in FIG. 9 includes a microphone 10 for picking up ambient sound; band-pass filters 21A, 21B, and 21C for only allowing signals in a specific frequency band to pass through; converters 22A, 22B, and 22C for comparing the signals which have passed through the band-pass filters 21A, 21B, and 21C with reference signals and for determining the levels of intensities of the signals; the analyzer 13; the database 14; and the output unit 15.

The band-pass filters 21A, 21B, and 21C are set relative to a plurality of different frequency bands in a low frequency band picked up by the microphone 10 during walking. For example, the band-pass filter 21A is set to a frequency band around the center frequency of 10 Hz; the band-pass filter 21B is set to a frequency band around the center frequency of 20 Hz; and the band-pass filter 21C is set to a frequency band around the center frequency of 30 Hz.

In the gait detection apparatus arranged as described above, when the microphone 10 picks up sound during walking, the band-pass filters 21A, 21B, and 21C extract low-frequency-band signals which are characteristic of walking. The comparators 22A, 22B, and 22C determine the levels of the signals from among three levels including "no signal detection", "low signal level", and "high signal level". The level determination is performed on the basis of threshold values which are set to the comparators 22A, 22B, and 22C, respectively.

The database 14 stores beforehand data for a table for distinguishing the gait pattern as shown in FIG. 10. Referring to FIG. 10, the symbol "-" represents "no signal detection"; the symbol "Δ" represents "low signal level"; and the symbol "o" represents "high signal level".

The analyzer 13 compares the signals in the frequency bands, whose levels are determined by the comparators 22A, 22B, and 22C, with the table as shown in FIG. 10, and specifies the corresponding gait patterns.

The gait detection apparatus shown in FIG. 9 with a simpler circuitry and simpler processing compared with the gait detection system shown in FIG. 1 can similarly detect the gait pattern. When at least one of the comparators 22A, 22B, and 22C determines that the signal level is "low signal level" or "high signal level", the analyzer 13 assumes this as one step and increases the count by one. Accordingly, the number of steps can be counted, and the gait cycle can be detected.

In the first embodiment, the pattern recognition technology required by the processes shown in FIGS. 6 and 7 can be achieved by appropriately using known technology or the like. Since this is not the primary object of the first embodiment of the present invention, a detailed description thereof is omitted.

Second Embodiment: Distance-Traveled Estimation

On the basis of the gait detection technology described in the first embodiment, a gait detection apparatus (gait detection system) for estimating the distance traveled by a pedestrian will now be described.

Figure 11:
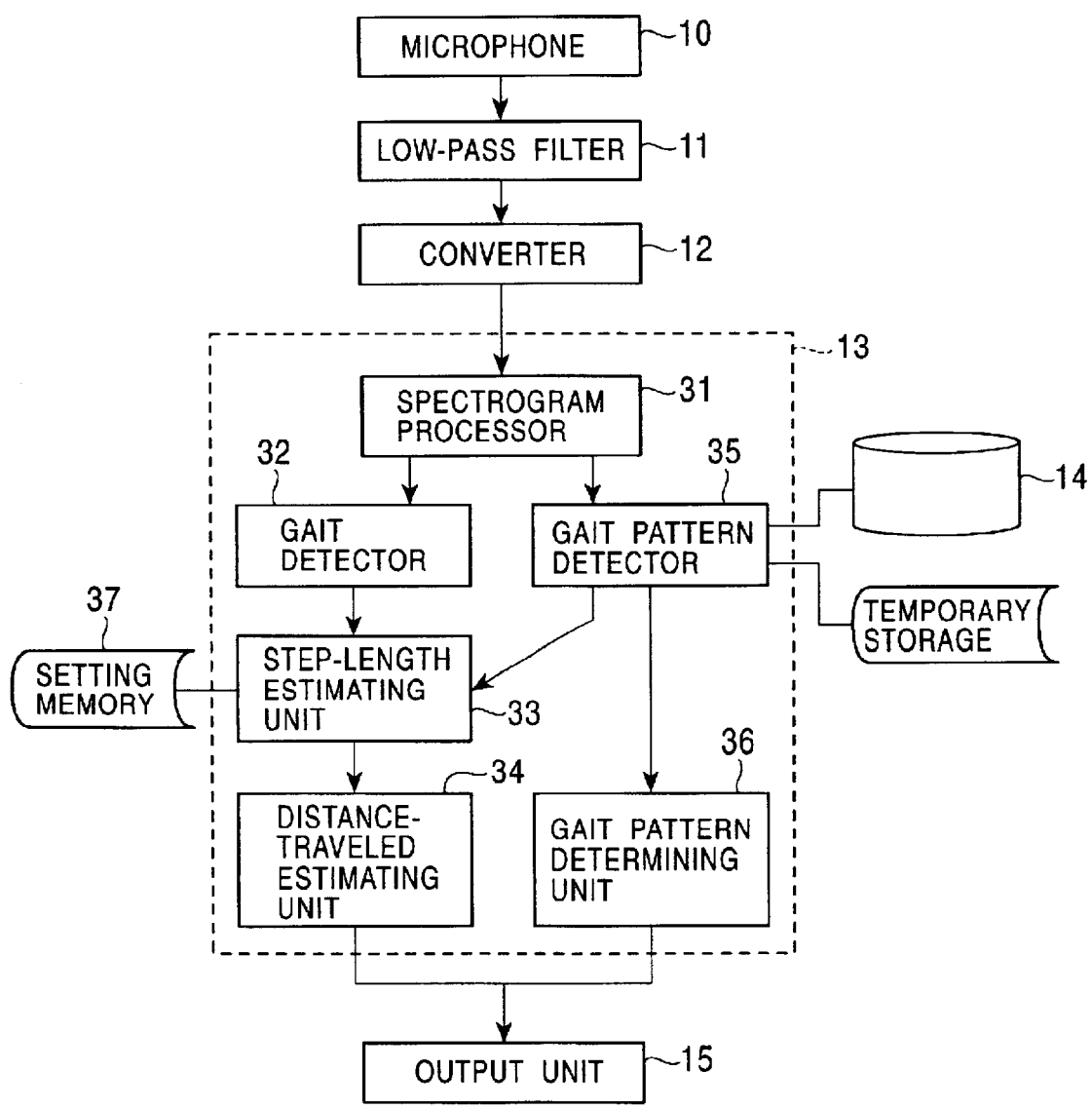
FIG. 11 is a block diagram showing the structure of a gait detection apparatus according to a second embodiment of the present invention.

Referring to FIG. 11, as is the case with the gait detection apparatus of the first embodiment, which is shown in FIG. 1, a gait detection apparatus of a second embodiment includes the microphone 10, the low-pass filter 11, the converter 12, the analyzer 13, the database 14 storing various gait pattern data, and the output unit 15.

The analyzer 13 includes a spectrogram processor 31 for generating a spectrogram on the basis of a signal converted by the converter 12; a gait detector 32 for detecting the gait of a pedestrian by performing processing similar to that shown in FIG. 7 in the first embodiment; a step-length estimating unit 33 for estimating step length; a distance-traveled estimating unit 34; a gait pattern detector 35 for detecting the gait pattern of the pedestrian by performing processing similar to that shown in FIG. 8 in the first embodiment; and a gait pattern determining unit 36 for determining the gait pattern of the pedestrian on the basis of the detection by the gait pattern detector 35.

In order to estimate step length by the step-length estimating unit 34, a process based on the detection by the gait detector 32 and the gait pattern detector 35 is performed.

One type of process includes detecting the walking frequency by the gait detector 32 and estimating step length on the basis of the walking frequency and the height of the pedestrian.

Figure 12:
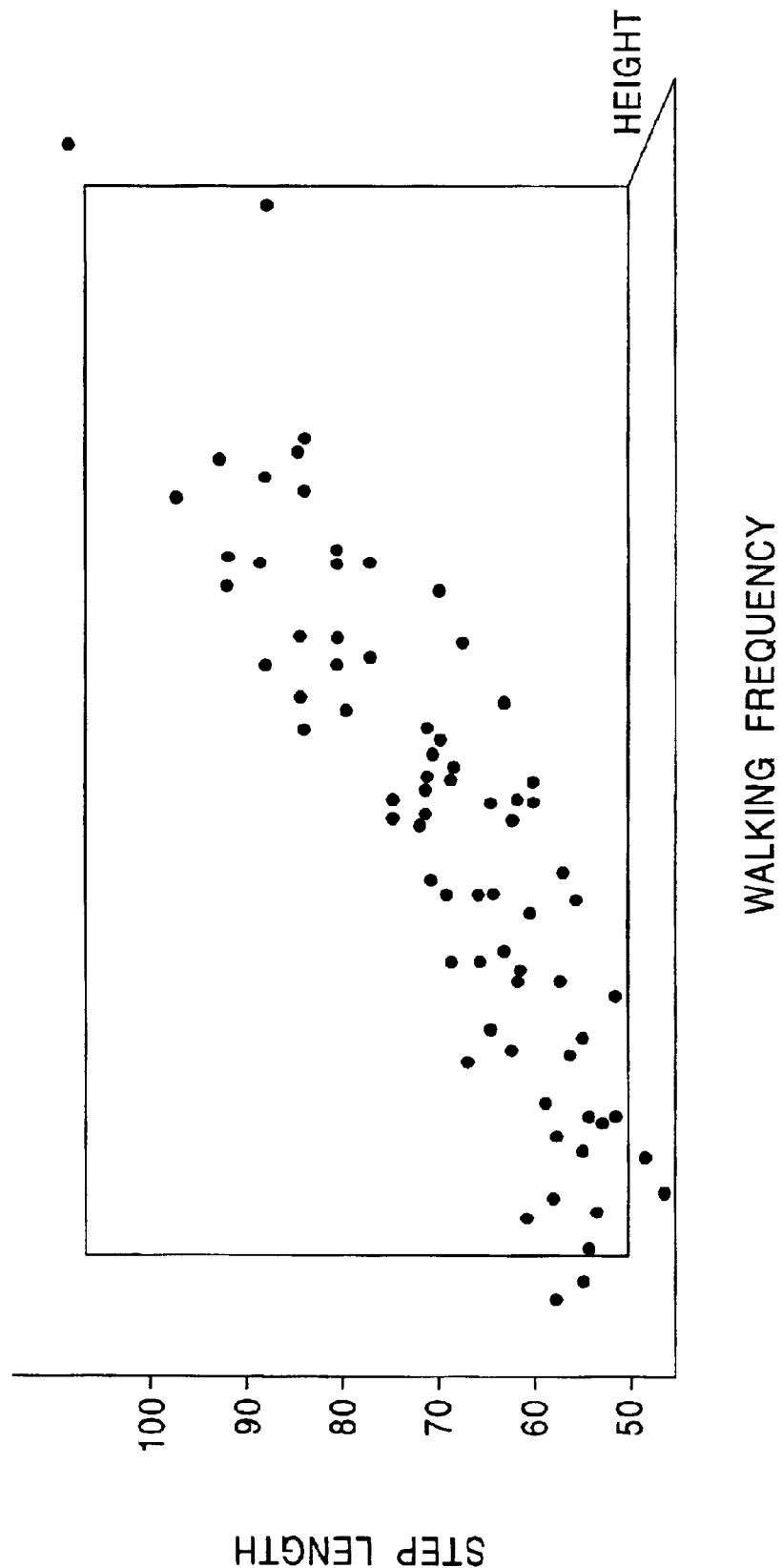
FIG. 12 is a data distribution diagram showing the relationships among a walking frequency, step length, and height.

In general, as shown in FIG. 12, it is well-known that the walking frequency, that is, the pace, and the pedestrian's height are correlated with the step length. FIG. 12 shows the relationship of the step length with the walking frequency and the height, which is plotted from a large number of test subjects. On the whole, the correlation of the step length with the walking frequency and the height is apparent.

In this case, the database 14 stores data for coefficients of relations among the walking frequency, the pedestrian's height, and step length. Prior to the gait detection, the height and the sex of the pedestrian are input to a setting memory 37.

Figure 13:
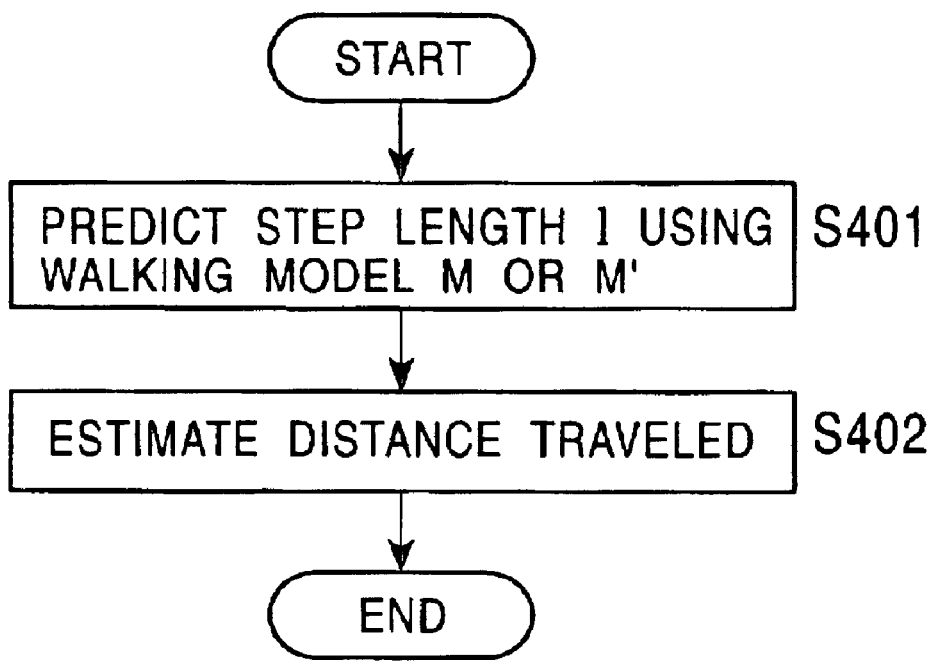
FIG. 13 is a flowchart of a process of estimating the distance traveled.

FIG. 13 shows a process of estimating step length. In step S401, the process estimates step length l using a walking model M on the basis of the gait cycle detected by the gait detector 32 and the pedestrian's height set to the setting memory 37. The walking model M can be expressed by:

$$\text{step length } l \text{ (cm)} = x1 \times \text{gait cycle(step/min)} + x2 \times \text{height (cm)} + C$$

In the above relational equation, x1, x2, and C are stored in advance in the database 14 and are coefficients and an initial value set for each gait pattern.

The distance-traveled estimating unit 34 integrates the length l obtained in this manner and the number of steps s per unit time which is detected by the gait detector 32, thereby estimating the distance traveled per unit time (step S402).

Although an example in which the process uses, in step S401, the relational equation of the gait model M has been described, the present invention is not limited to this example. For example, the relational equation of the gait model M can be determined on the basis of the ratio of energy at the time the heal strikes the ground to energy at the time of toe-off.

Figure 14:
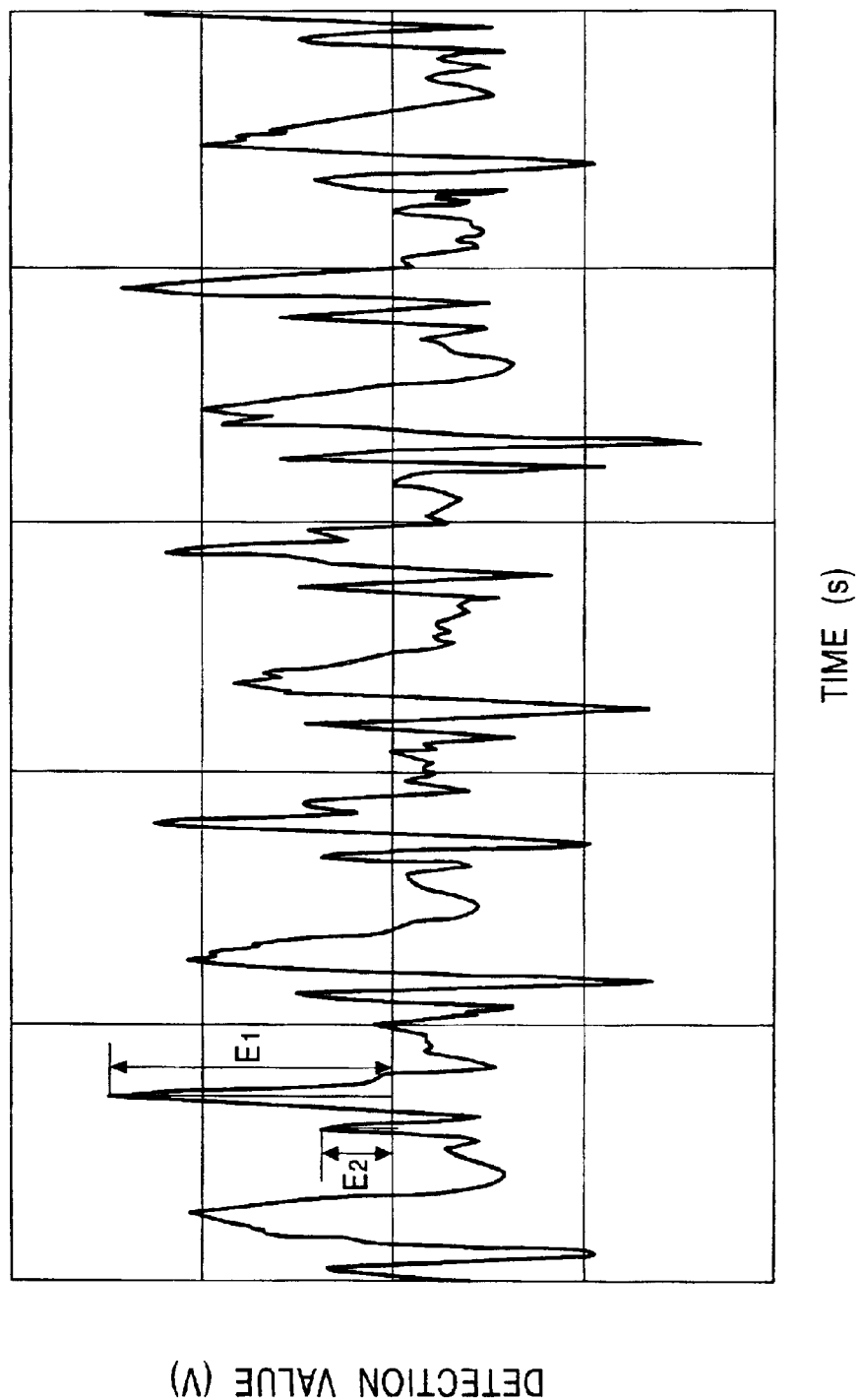
FIG. 14 is a graph showing variations in energy during walking.

FIG. 14 shows variations in energy during walking. Propulsion energy $E_1$ which is energy at the time of toe-off is a peak value of a gait signal. Heel-strike energy $E_2$ at the time the heel strikes the ground is the maximum value immediately before the peak value corresponding to the propulsion energy $E_1$. The heel-strike energy $E_2$ divided by the propulsion energy $E_1$ is the touchdown-propulsion energy ratio.

On the basis of the touchdown-propulsion energy ratio thus obtained, the gait cycle detected by the gait detector 32, and the pedestrian's height set to the setting memory 37, the step length l can be estimated using a walking model M'.

The walking model M' can be expressed by:

$$\text{step length } l \text{ (cm)} = x1 \times \text{gait cycle(step/min)} + x2 \times \text{height (cm)} + x3 \times \text{touchdown-propulsion energy ratio}$$

In this relational equation, x1, x2, and x3 are coefficients for each gait pattern, which are stored in advance in the database 14.

Another method of estimating step length by the step-length estimating unit 33 uses variations in the frequency intensity as a result of the impact made by the heel or toe striking the ground.

In a human gait pattern, when the pedestrian walks at a fast pace, both the walking frequency and the step length increase. When the pedestrian consciously walks with large strides, the step length varies whereas the walking frequency remains unchanged. When the pedestrian travels a long distance, the step length is an approximately constant value which is determined on the basis of the height and the pace. When the pedestrian travels a short distance or in a different mood, the step length easily changes.

In order to prevent effects of such factors, as shown in FIG. 2, the frequency intensity in the normal gait is stored beforehand as a reference value in the database 14. By comparison with the reference value, increase/decrease in the impact at the time the heel/toe strikes the ground is detected, and the step length is corrected.

Figure 15:
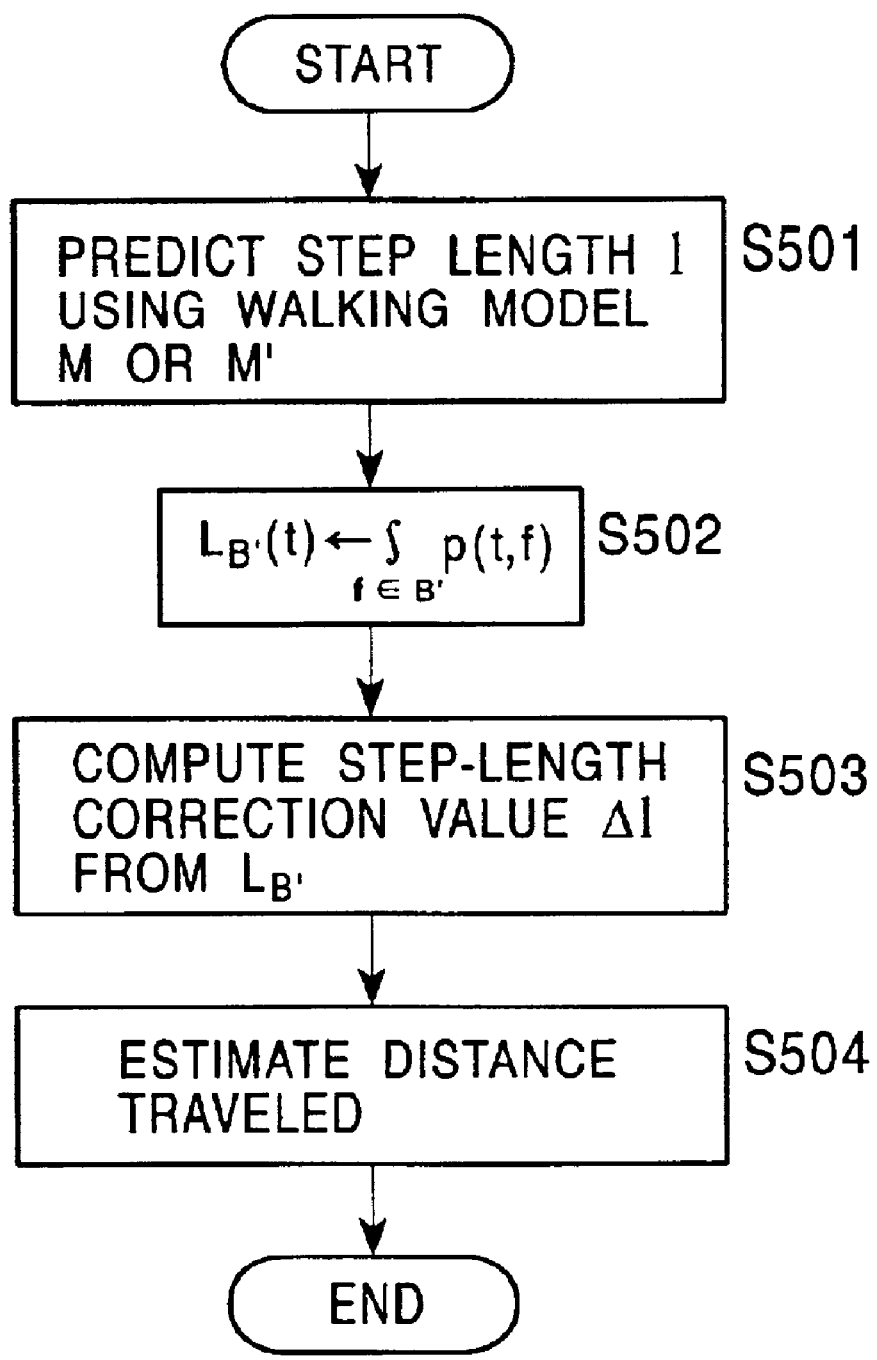
FIG. 15 is a flowchart showing another process of estimating the distance traveled.

FIG. 15 shows the specific flow of the foregoing process. Similarly to step S401 in FIG. 13, the process estimates step length l using the walking model M or M' on the basis of the gait cycle detected by the gait detector 32 and the pedestrian's height set to the setting memory 37 (step S501).

The process integrates a relational expression p(t, f) of the time and frequency, which is obtained in a manner similar to steps S201 and S202 in FIG. 7, relative to a frequency band B' in which the touchdown impact can be characteristically extracted, thus obtaining a touchdown impact $L_{B'}$ (step S502). By integrating the relational expression p(t, f), the occupancy ratio of signals of the spectrogram in the frequency band B' can be detected.

On the basis of a table or relational equation stored in advance in the database 14, a step-length correction value Δl is computed from the impact $L_{B'}$ (step S503). Using the step-length correction value Δl, the distance traveled (1×s+Δl) is obtained (step S504).

Accordingly, the step length can be corrected on the basis of the frequency intensity of the spectrogram.

Another method of estimating step length by the step-length estimating unit 33 uses the frequency intensity at the time of toe-off and the frequency intensity at the time of toe-strike. Specifically, when the pedestrian walks at a constant pace, the step length may differ according to the toe-off strength. In accordance with the intensity of a frequency band of approximately 10 to 16 Hz, which occurs in accordance with the toe-strike and the toe-off, comparison is performed using a reference value of the frequency intensity of the pedestrian, which is stored beforehand in the database 14, and gait history data. Accordingly, the step length is corrected.

Figure 16:
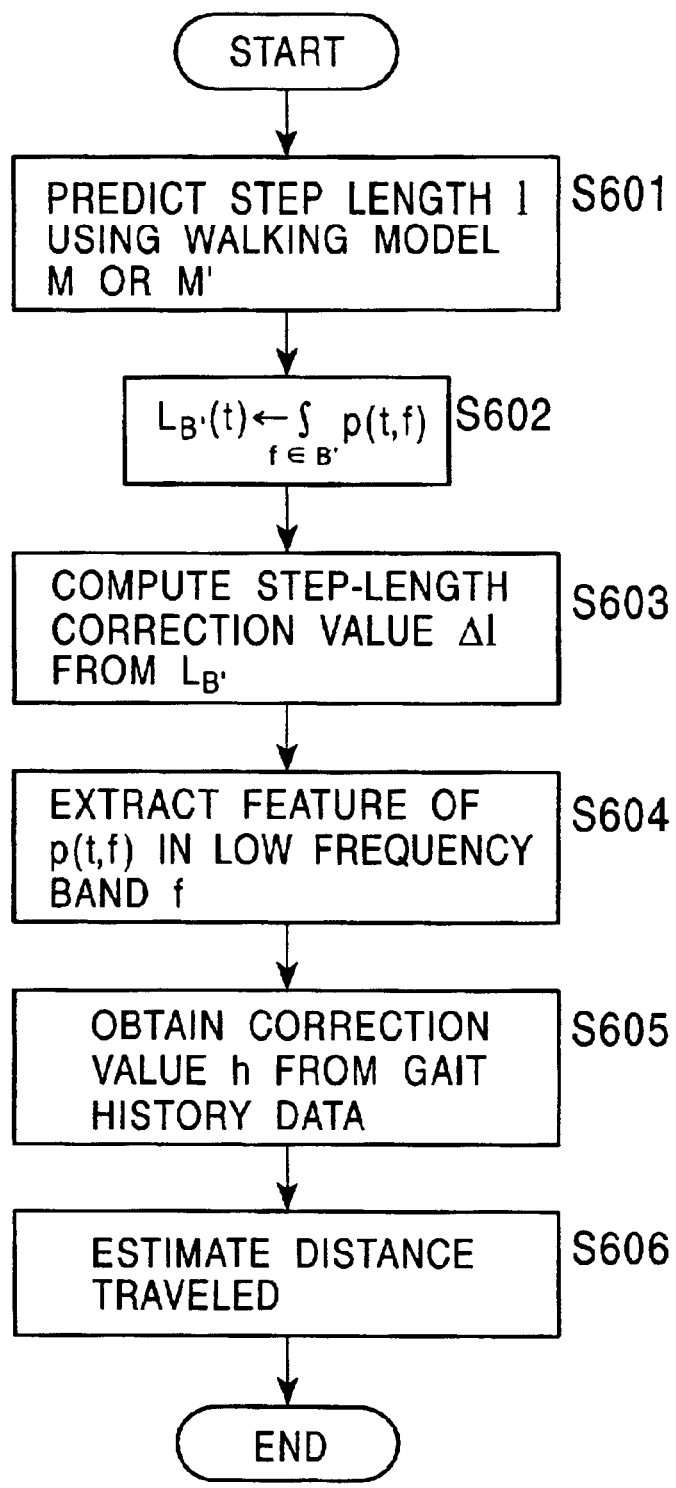
FIG. 16 is a flowchart showing another process of estimating the distance traveled.

FIG. 16 shows the flow of the process. Similarly to steps S501 to S503 in FIG. 15, the process estimates step length l using the walking model M or M' on the basis of the gait cycle detected by the gait detector 32 and the pedestrian's height set to the setting memory 37 (step S601). Subsequently, the process integrates the time/frequency-intensity relational expression p(t, f) relative to the frequency band B' in which the touchdown impact can be characteristically extracted, thus obtaining the touchdown impact $L_{B'}$ (step S602). On the basis of the table or relational equation stored in advance in the database 14, the step-length correction value Δl is computed using the impact $L_{B'}$ (step S603).

Subsequently, the analyzer 13 extracts a feature of the relational expression p(t, f) for the predetermined low-frequency band f (for example, 0 to 40 Hz) (step S604).

On the basis of feature pattern data for the frequency intensity and the pedestrian's reference value and gait history data, a step-length correction value h is obtained (step S605).

Subsequently, the distance traveled (1×s+Δl+h) can be obtained using the correction value h (step S606).

Accordingly, the step length can be estimated on the basis of the gait cycle detected by the gait detection apparatus and the pedestrian's height. Using the signals detected during walking, the step length can be estimated more accurately. The gait cycle can be detected when the step is the second step or a subsequent step. Variations in the pace can be detected in real time. Therefore, the step length can be detected with high accuracy.

The step length estimated by such a gait detection apparatus can be used as data for correcting the location by a navigation system or data for autonomous navigation. It is thus preferable that the gait detection apparatus be connected to or be included in a navigation apparatus.

Third Embodiment: Person Authentication

A gait detection apparatus (gait detection system) for detecting the gait of a pedestrian, as in the first embodiment, and for identifying the pedestrian on the basis of the pedestrian's gait pattern will now be described.

Figure 17:
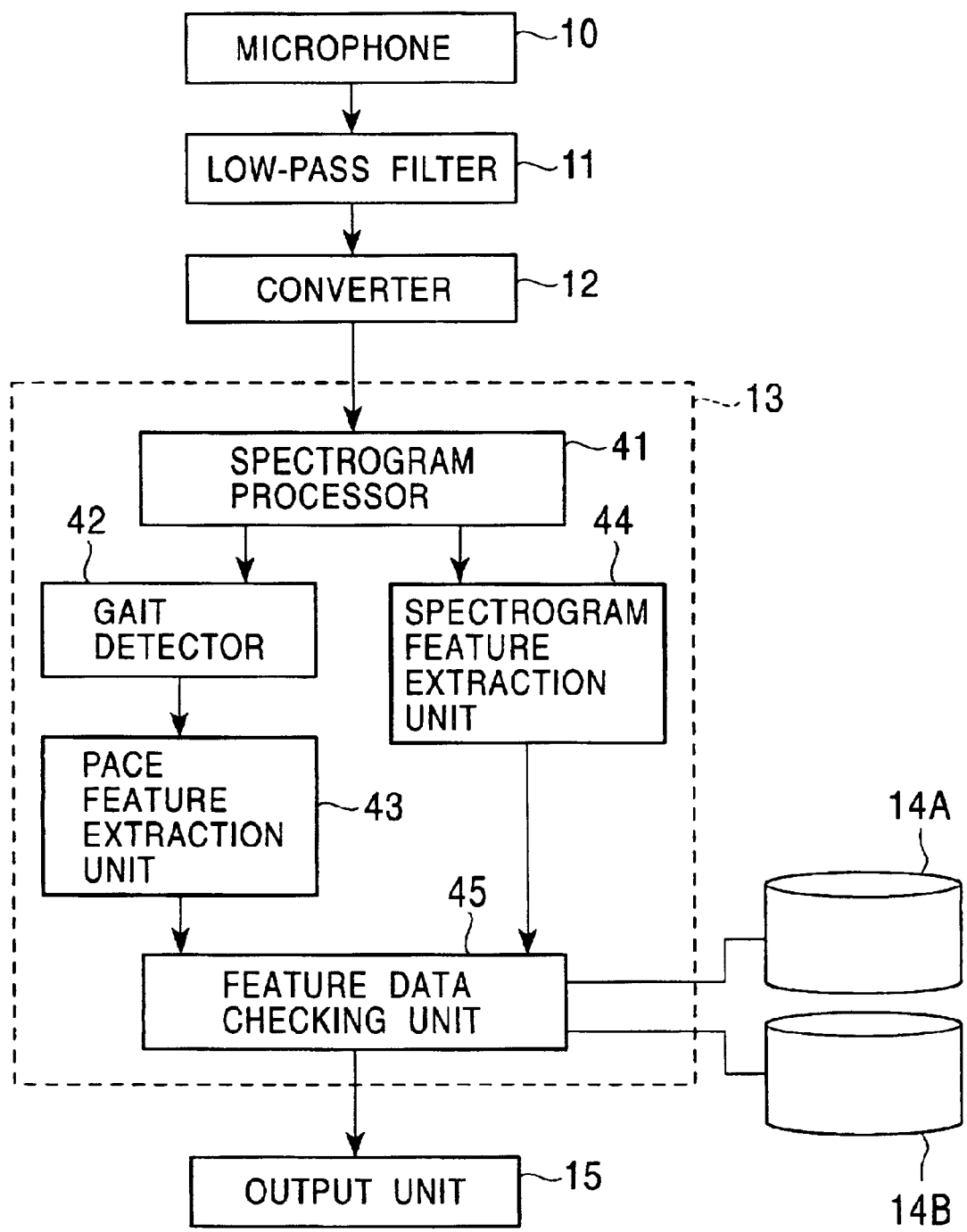
FIG. 17 is a block diagram showing the structure of a gait detection apparatus according to a third embodiment of the present invention.

Referring to FIG. 17, as is the case with the gait detection apparatus of the first embodiment, which is shown in FIG. 1, a gait detection apparatus of a third embodiment includes the microphone 10, the low-pass filter 11, the converter 12, the analyzer 13, databases (data storage devices) 14A and 14B storing various gait pattern data, and the output unit 15.

The analyzer 13 includes a spectrogram processor 41 for generating a spectrogram on the basis of a signal converted by the converter 12; a gait detector 42 for detecting the gait of a pedestrian by performing processing similar to that shown in FIG. 7 in the first embodiment; a pace feature extraction unit 43 for extracting features of a pace on the basis of the detected gait; a spectrogram feature extraction unit 44 for extracting time/frequency/intensity features on the basis of the spectrogram; and a feature data matching unit 45 for checking the feature data extracted by the pace feature extraction unit 43 and the spectrogram feature extraction unit 44 with the data stored in the databases 14A and 14B and for determining whether the feature data match the stored data.

In the databases 14A and 14B, personal feature data for the pedestrian is stored in advance. When the pedestrian to be registered walks for a predetermined period of time, feature data is extracted by the pace feature extraction unit 43 and the spectrogram feature extraction unit 44. The extracted feature data is stored in the databases 14A and 14B. It is preferable that the stored feature data be related with personal identification data, such as the name, number, or the like, for identifying the pedestrian. Speech recognition technology can be applied to extract features of the spectrogram.

In the database 14A, features of patterns plotted by time/frequency/intensity of signals during walking are stored for each person. During walking, as is the case with voices, individuals have unique features based on walking features and physiques such as bones, joints, and muscles. Therefore, spectrograms generated by the spectrogram processor 41 in response to ground-contact made with the foot soles differ among individuals, as shown in FIG. 4. By analyzing the time/frequency/intensity of the spectrogram, the patterns plotted by the time/frequency/intensity can be collected as data, and the data can thus be stored in the database 14A.

In the database 14B, features of walking rhythm specific to each pedestrian are stored. Specifically, data on the stance-phase time of the left leg and the right leg (portions (2) and (3) in FIG. 2) and data on the gap time (portions (4) and (5) in FIG. 2) during walking are stored as data on walking rhythm specific to each individual in the database 14B.

Referring to FIG. 18, in the gait detection apparatus, the microphone 10 picks up low-frequency-region components generated by a pedestrian while walking. From the obtained signals w(t), the low-pass filter 11 eliminates signals at or higher than a predetermined frequency, that is, normal audio signals, thus obtaining signals w'(t) (step S701).

In the analyzer 13, the spectrogram processor 41 generates a spectrogram of the signals w'(t). The spectrogram feature extraction unit 44 extracts time/frequency/intensity features of the spectrogram. Alternatively, as in step S301 in FIG. 8, gait features can be extracted from the relational expression p(t, f) of the time, frequency, and intensity.

Simultaneously, the gait detector 42 performs processing similar to that shown in FIG. 7 in the first embodiment and detects the gait of the pedestrian. The pace feature extraction unit 43 generates data on the stance-phase time (portions (2) and (3) in FIG. 2) and the gap time (portions (4) and (5)) from the detected gait and extracts features of the pace (step S702).

The feature data checking unit 45 checks the feature data extracted by the pace feature extraction unit 43 and the spectrogram feature extraction unit 44 against the data stored in the databases 14A and 14B and determines whether or not the former data correspond to the latter data (step S703).

If there is data that correspond to the data stored in the databases 14A and 14B, it is determined that the pedestrian is a pre-registered pedestrian, and the pedestrian is identified (step S704). However, when there is no data corresponding to the data stored in the databases 14A and 14B, it is determined that the pedestrian is an unregistered pedestrian. Subsequently, the output 15B outputs data for the pedestrian authentication result.

With the gait detection apparatus of the third embodiment, the pedestrian can be identified on the basis of low-frequency-region components picked up by the microphone 10 while the pedestrian is walking. Since it is possible to determine whether or not the pedestrian is a registered pedestrian, the gait detection apparatus can be used for person authentication.

For example, the gait detection apparatus of the third embodiment can be incorporated in a portable apparatus with the microphone 10, such as a cellular-phone-type terminal or a wireless apparatus. On the basis of sound, i.e., vibrations, picked up by the microphone 10 while the pedestrian is walking, it is possible to determine whether or not the pedestrian who has the apparatus is a pre-registered, valid user. If it is determined that the pedestrian is an invalid user, the cellular-phone-type terminal or the wireless apparatus can be disabled or prohibited from sending signals. A predetermined signal can be output to automatically notify that the apparatus is possessed by the invalid user. By loading a program in accordance with the contents of these functions, these functions can be implemented.

Figure 19A:
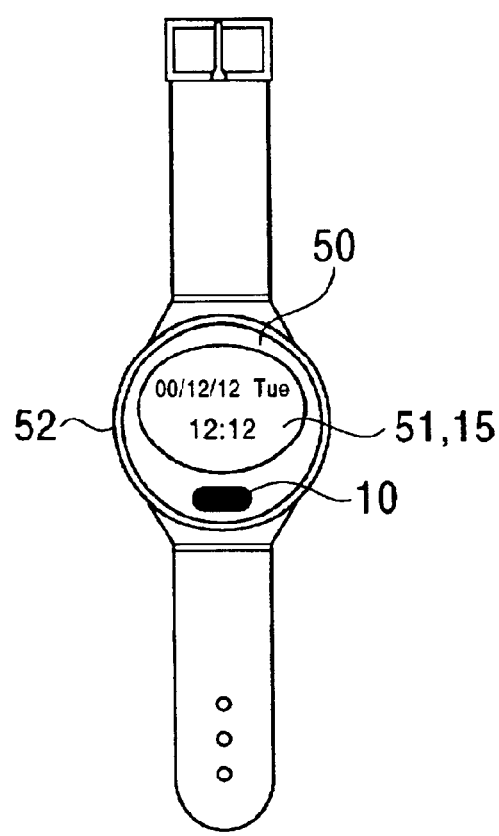
FIGS. 19A and 19B illustrate examples of devices as a gait detection apparatus, including FIG. 19A showing a wristwatch and FIG. 19B showing a cellular-phone-type terminal as a gait detection apparatus.
Figure 19B:
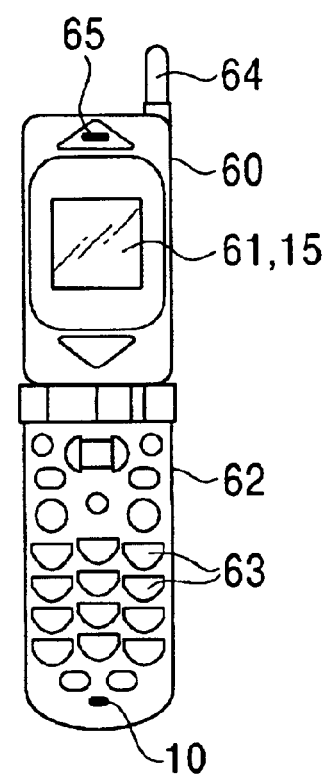

FIGS. 19A and 19B show specific examples of devices as the gait detection apparatuses described in the foregoing embodiments.

FIG. 19A shows a wristwatch 50 (gait detection apparatus or device) which can be worn by a user on his/her arm. The wristwatch 50 includes the microphone 10 which is provided on the external surface thereof and a display screen or display unit 51 which functions as the output unit 15. The low-pass filter 11, the converter 12, the analyzer 13, and the database 14, all of which are shown in FIG. 1, or the band-pass filters 21A, 21B, and 21C, the comparators 22A, 22B, and 22C, the analyzer 13, the database 14, etc, all of which are shown in FIG. 9, are housed in a casing 52 of the wristwatch 50. An operation unit for operating the wristwatch 50 is provided on the surface of the casing 52.

The wristwatch 50 includes a clock for time-keeping of the wristwatch 50, a display controller for controlling display by the display screen 51, etc (now shown in FIG. 19A) in the casing 52. The time generated by the clock is displayed on the display screen 51. Also, unit-time information which is required to detect the gait cycle or the like by the analyzer 13 can be obtained from the clock.

With the wristwatch 50, as described above, gait detection can be performed. For example, only the number of steps can be detected. Accordingly, the wristwatch 50 can include a pedometer function for counting the number of steps. Alternatively, the gait cycle and other information can be detected. The detected information can be displayed on the display screen 51 using characters and the like.

Since an acceleration sensor, a gyro sensor, a pendulum, and the like are unnecessary, the size of the wristwatch 50 does not have to be large. Since the gait is detected on the basis of sound, i.e., vibrations, which are picked up the microphone 10, the setting of the wristwatch 50 on the pedestrian is not restricted as in a conventional type; it is only required that the wristwatch 50 be positioned near the body of the pedestrian so that the vibrations generated during walking can be picked up. In other words, it is only necessary for the pedestrian to wear the wristwatch 50 on the arm.

FIG. 19B shows a cellular-phone-type terminal 60 (gait detection apparatus or device). On the external surface, the microphone 10 and a display screen 61 as the output unit 15 are provided. The low-pass filter 11, the converter 12, the analyzer 13, and the database 14, all of which are shown in FIG. 1, or the band-pass filters 21A, 21B, and 21C, the comparators 22A, 22B, and 22C, the analyzer 13, the database 14, etc, all of which are shown in FIG. 9, are stored in a casing 62 of the cellular-phone-type terminal 60.

In the casing 62, an operation unit 63 for operating the cellular-phone-type terminal 60, an antenna 64 for transmitting/receiving electromagnetic waves, and a speaker 65 for outputting audio are provided. Furthermore, the casing 62 houses a data converter for coding/decoding electromagnetic waves transmitted/received by the antenna 64, an audio converter for converting data into audio, and a controller for controlling the overall cellular-phone-type terminal 60 (all of which are not shown) for achieving telephone communication functions. It is preferable that the cellular-phone-type terminal 60 be mounted on pedestrian's clothes such as a belt.

With the cellular-phone-type terminal 60, gait detection can be performed to detect the number of steps and the gait cycle, and the detection information can be displayed on the display screen 61 using characters and the like. Since the cellular-phone-type terminal 60 already has the microphone 10 for telephone messages, it is not necessary to provide the additional microphone 10. The size of the cellular-phone-type terminal 60 does not have to be increased, and a gait detection function can be added at low cost. Thus, the cellular-phone-type terminal 60 becomes a high value-added apparatus.

In the foregoing embodiments, the gait detection apparatus can be of any configuration. For example, it is unnecessary that the microphone 10, the analyzer 13, and the output unit 15 are integrated. For example, when the microphone 10 is set on a pedestrian to be detected, signals of vibrations (sounds) picked up by the microphone 10 can be transmitted to the analyzer 13 side via a connecting cord or wireless communication means using electromagnetic waves, infrared rays, etc. Another configuration can be employed in which the microphone 10 of a cellular-phone-type terminal picks up vibrations (sounds) generated during walking and the vibrations are transmitted to the analyzer 13 located at a different place via a public telephone line or the like using a communication function of the cellular-phone-type terminal. In another configuration, the microphone 10 and the analyzer 13 are set on the pedestrian; obtained data is transmitted to the output unit 15 via a connecting cord or wireless communication means using electromagnetic waves, infrared rays, etc.; the data is output from the output unit 15.

These system configurations are useful for setting the microphone 10 on a patient at a medical institution or the like and analyzing, by a doctor or the like, gait sounds generated by the patient, i.e., the pedestrian. In a known system for collecting gait data from a patient at a medical institution or the like, a pressure-sensitive mat is laid down, or shoes with pressure-sensitive mats attached to the soles are employed. In this way, the pedestrian can only walk on a limited area. In contrast, as arranged as described above, the patient can freely walk at any place.

In the field of biometrics, the system arranged as described above is useful for dynamically distinguishing an object such as a person or an animal while the object is walking.

The gait detection apparatus or the microphone thereof is not limited to the wristwatch 50 or the cellular-phone-type terminal 60 illustrated in the foregoing examples, and it can be applied to another portable device. For example, the gait detection apparatus can be applied to a wristwatch-type pedometer without a clocking function.

The invention is intended to cover various modifications and equivalent arrangements included within the spirit and scope of the appended claims.

What is claimed is:

1. A gait detection system comprising:

a microphone for picking up vibrations generated by a pedestrian while walking and for converting the vibrations into electrical signals;

analysis means for analyzing variations corresponding to a frequency less than or equal to a predetermined frequency of the electrical signals converted by the microphone, for detecting a gait of the pedestrian, and for generating information on the detected gait; and output means for outputting the information on the detected gait.

2. The gait detection system according to claim 1, wherein the analysis means determines a pattern of the gait of the pedestrian based on at least one of a duration and a frequency intensity of a signal in a frequency band less than or equal to 100 Hz.

3. The gait detection system according to claim 1, wherein the analysis means estimates a stride length of the pedestrian based on a gait cycle detected by the analysis means and a pre-input height of the pedestrian.

4. The gait detection system according to claim 3, wherein the analysis means estimates a distance traveled by the pedestrian based on the stride length and a number of steps detected by the analysis means.

5. A gait detection apparatus comprising:

analysis means for analyzing a frequency component of a signal based on a vibration transmitted through the body of a pedestrian while walking and for detecting a gait of the pedestrian; and output means for outputting information on the gait detected by the analysis means.

6. The gait detection apparatus according to claim 5, further comprising a filter for passing only a signal in a predetermined frequency band, wherein the analysis means detects the gait of the pedestrian based on a presence or absence of the signal having passed through the filter.

7. The gait detection apparatus according to claim 5, further comprising data storage means for storing signal data corresponding to a gait model pattern, wherein the analysis means analyzes a signal by comparing the signal with the signal data stored in the data storage means and by determining whether a pattern of the signal detected by the analysis means matches the signal data.

8. A device to be mounted on a user, comprising:

a microphone for picking up ambient sounds and for converting the ambient sounds into electrical signals:

analysis means for analyzing variations in signals corresponding to a frequency less than or equal to a predetermined frequency based on the electrical signals converted by the microphone and for detecting a gait of the user; and display means for outputting information concerning the gait detected by the analysis means using characters.

9. The device according to claim 8, wherein the analysis means detects a number of steps walked by the user.

10. A gait detection method comprising the steps of:

detecting components in a frequency band less than or equal to 100 Hz from vibrations transmitted through the body of a pedestrian while walking; and converting the detected components into signals and analyzing the signals, wherein a gait of the pedestrian is detected.

* * * * *